(12) United States Patent
Dodds et al.

(10) Patent No.: US 6,521,445 B1
(45) Date of Patent: Feb. 18, 2003

(54) PROCESS FOR PREPARING OPTICALLY ACTIVE GLYCIDATE ESTERS

(75) Inventors: David Richard Dodds, Millis, MA (US); Jorge Luis Lopez, Framingham, MA (US); Charles Melvyn Zepp, Berlin, MA (US); Steven Brandt, Marlborough, MA (US)

(73) Assignee: Sepracor, Inc., Marlborough, MA (US)

( * ) Notice: Subject to any disclaimer, the term of this patent is extended or adjusted under 35 U.S.C. 154(b) by 0 days.

(21) Appl. No.: 07/335,636

(22) Filed: Apr. 10, 1989

Related U.S. Application Data

(63) Continuation-in-part of application No. 07/309,769, filed on Feb. 10, 1989, now Pat. No. 5,274,300, which is a continuation-in-part of application No. 07/265,171, filed on Oct. 26, 1988, now abandoned.

(51) Int. Cl.⁷ .............. C12P 7/62; C12P 7/40
(52) U.S. Cl. .......... 435/280; 435/135; 435/136; 435/155; 435/132
(58) Field of Search ............... 435/280, 135, 435/136, 155, 132

(56) References Cited

U.S. PATENT DOCUMENTS 4,732,853 A * 3/1988 Whitesides et al. ......... 435/123

FOREIGN PATENT DOCUMENTS

| EP | 0158339 | * 10/1985 |
| EP | 0264457 | * 10/1987 |
| EP | 0343714 | * 11/1989 |
| EP | 0362556 | * 4/1990 |

OTHER PUBLICATIONS

Ladner et al, J. Am. Chem. Soc., 106, 7250–7251, 1984.*
Laane et al, Elsevier Science Publishers B.V., Netherlands, 279–284, 1987.*
Schneider et al, Angew. Chem. Int. Ed. Eng., 23(1) 64–66, 66 and 67–68, 1984.*
Iriuchijima et al, Agrc. Biol. chem., 46(6), 1593–1597, 1982.*
Ito et al, J. Am. Chem. Soc., 103, 6739–6741, 1981.*
Lavayre et al, Biotech. Bioeng., 24, 2175–2197, 1982.*
Sugita et al, J. Biochem., 87, 339–341, 1980.*
Tang, J. Biol. Chem, 246(14), 4510–4517, 1971.*
McCaul et al, Biochem. Biophys. Res. Commun., 72(3), 1028–1034, 1976.*
Sabbioni, Jo. Org. Chem., 52:4565–4570, 1987.*

* cited by examiner

Primary Examiner—Shailendra Kumar
(74) Attorney, Agent, or Firm—Pennie & Edmonds LLP

(57) ABSTRACT

This invention relates to a method for the production of (2R,3S)-3-(4-methoxyphenyl)glycidic acids and esters thereof, which are synthetic intermediates for the production of the calcium antagonist diltiazem. The method involves the stereoselective enzymatic ester hydrolysis of racemic trans-3-(4-methoxyphenyl)glycidic acid ester to yield the resolved (2R,3S) compound as the ester. Membrane reactor methods and apparatus for the conduct of this enzymatic resolution process are also disclosed herein, as is the use of bisulfite anion in the aqueous reaction phase as a means of minimizing the inhibitory effect of an aldehyde reaction by-product on the reaction's progress. The benefits of selected solvent systems from which may be obtained highly resolved ester product are also disclosed. These enriched organic solutions may be used in subsequent transformations. Alternatively, optically pure product may be obtained directly therefrom.

72 Claims, 10 Drawing Sheets

Figure 1:
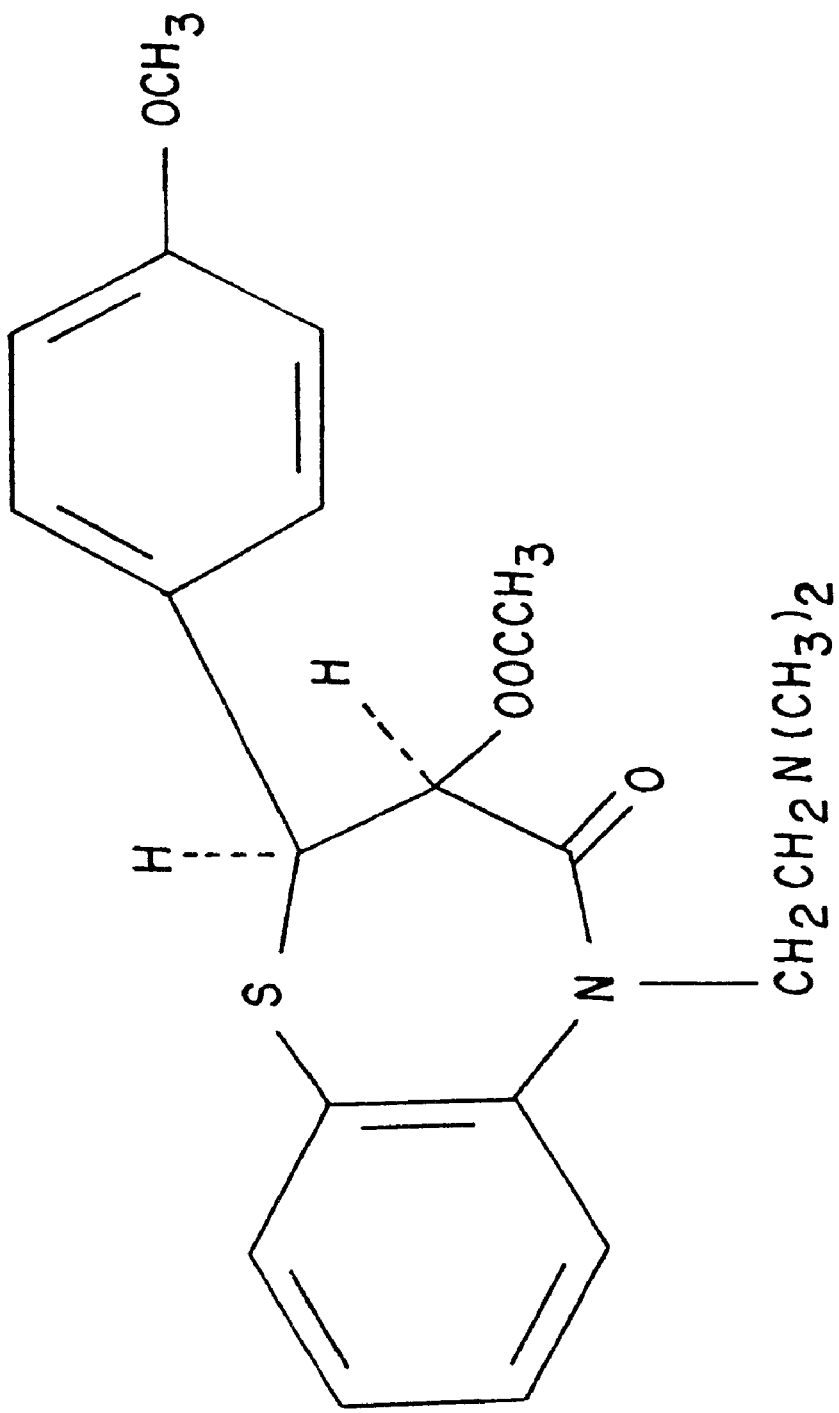

FIG. 4
TRANS-3-(4-METHOXYPHENYL) GLYCIDIC ACID ESTER.
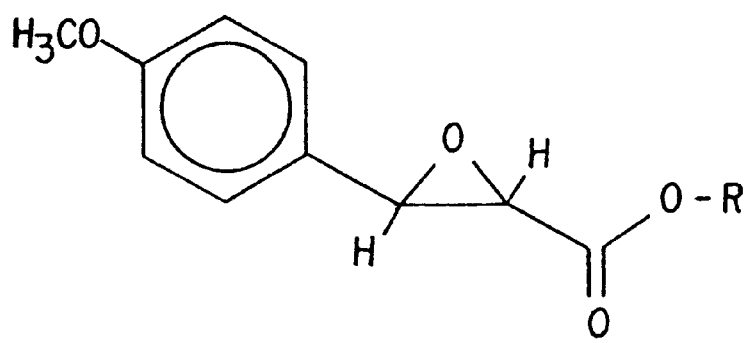
CIS-3-(4-METHOXYPHENYL) GLYCIDIC ACID ESTER
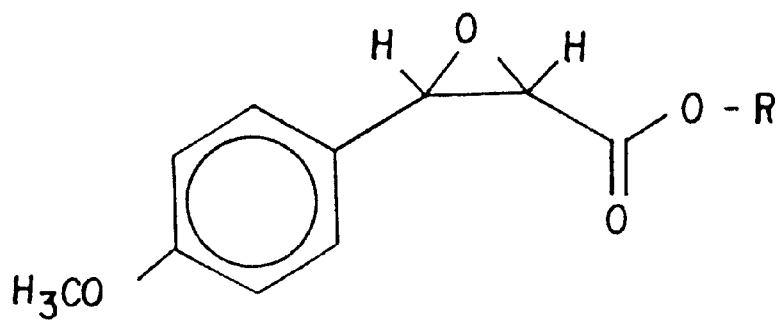

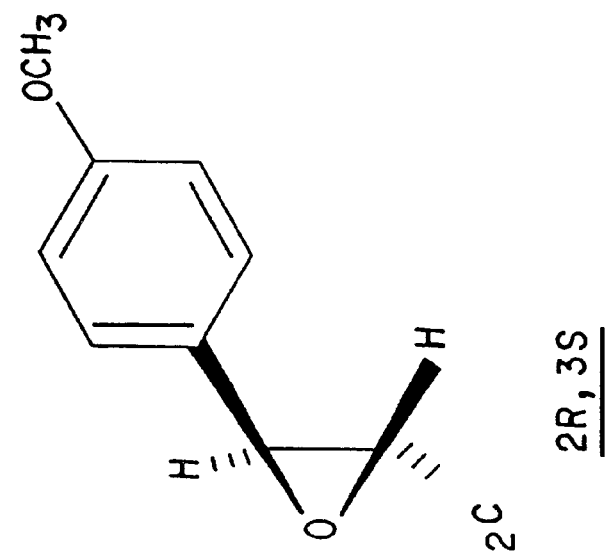
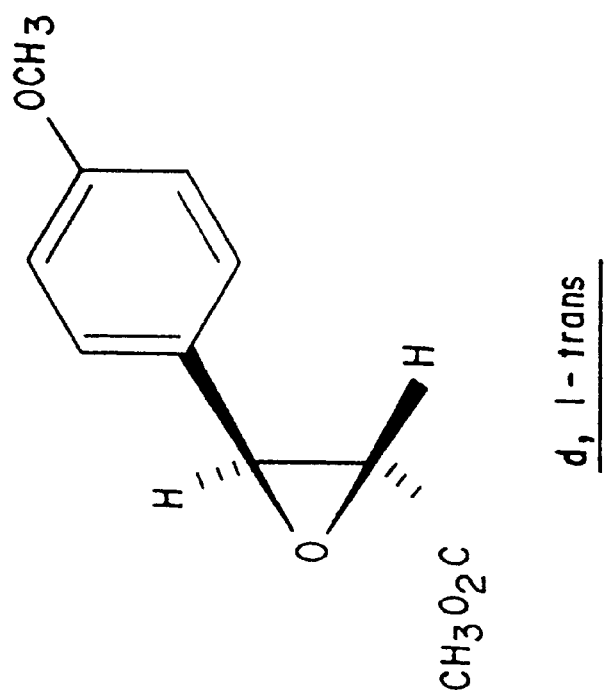
FIG. 5

MULTIPHASE / EXTRACTIVE MEMBRANE BIOREACTOR FOR ENZYMATIC RESOLUTION OF A DILTIAZEM PRECURSOR

PROCESS FOR PREPARING OPTICALLY ACTIVE GLYCIDATE ESTERS

The present application is a continuation-in-part of prior U.S. application Ser. No. 07/309,769, filed Feb. 10, 1989, now U.S. Pat. No. 5,274,300, which in turn, is a continuation-in-part of prior U.S. application Ser. No. 07/265,171 now abandonded, entitled "Process for Preparing Optically Active Glycidate Esters," filed Oct. 26, 1988. The complete disclosures of these co-pending U.S. Applications are incorporated by reference herein.

TABLE OF CONTENTS

1. Introduction
2. Background of the Invention
   2.1. Diltiazem and its Analogues
   2.2. The Stereochemistry of Diltiazem and Its Precursors
   2.3. Techniques for Resolution of Glycidate Esters
   2.4. Enzymatic Resolution of Racemic Mixtures
3. Summary of the Invention
4. Brief Description of the Figures
5. Detailed Description of the Invention
   5.1. Multiphase Enzymatic Reaction Processes
   5.2. Examples of Multiphase Enzymatic Resolutions
      5.2.1. Procedures for Examples 1–6
      5.2.2. Example 1—Stereoselective Hydrolysis of trans-3-(4-methoxy-phenyl)glycidic Acid Methyl Ester in tert-butyl Methyl Ether
      5.2.3. Example 2—Stereoselective Hydrolysis of trans-3-(4-methoxy-phenyl)glycidic Acid Methyl Ester in Toluene
      5.2.4. Example 3—Stereoselective Hydrolysis of trans-3-(4-methoxy-phenyl)glycidic Acid Ethyl Ester in tert-butyl Methyl Ether
      5.2.5. Example 4—Stereoselective Hydrolysis of trans-3-(4-methoxy-phenyl)glycidic Acid n-Butyl Ester in tert-Butyl Methyl Ether
      5.2.6. Example 5—Stereoselective Hydrolysis of trans-3-(4-methoxy-phenyl)glycidic Acid Isopropyl Ester in tert-Butyl Methyl Ether
      5.2.7. Example 6—Stereoseletive Hydrolysis of trans-3-(4-methoxy-phenyl)glycidic Acid Isobutyl Ester in tert-Butyl Methyl Ether
      5.2.8. Effect of Cosolvent on Apparent Enantioselectivity E: Example 7
      5.2.9. Effect of Water-Immiscible Organic Solvent on Apparent Enatio-selectivity E: Example 8
      5.2.10. Effect of pH on Enzyme Enatio-selectivity E: Example 9
      5.2.11. Methyl Ester Hydrolysis Catalyzed by Lipase MAP—Examples 10 and 11
      5.2.12. Methyl Ester Hydrolysis Catalyzed by Lipase-OF—Example 12
      5.2.13. Resolution of Racemic Methyl 3-(4-Methoxyphenyl)-glycidate in a Membrane Reactor at pH 7— Example 13
      5.2.14. Resolution of Racemic Methyl 3-(4-Methoxyphenyl)-glycidate in a Membrane Reactor at pH 8— Examples 14–17
   5.3. Management of the Aldehyde Byproduct by Adduct Formation with Bisulfite
   5.4. Examples Pertinent of Bisulfite Utilization
      5.4.1. Resolution of trans-3-(4-Methoxy-phenyl) glycidic Acid Methyl Ester in a Multiphase Enzyme Membrane Reactor
      5.4.2. Example 18—resolution of trans-3-(4-Methoxyphenyl)glycidic Acid Methyl Ester in a Multiphase Enzyme Membrane Reactor in the Absence of Bisulfite
      5.4.3. Example 19—Resolution of trans-3-(4-Methoxyphenyl)glycidic Acid Methyl Ester in a Multiphase Enzyme Membrane Reactor Using Sodium Bisulfite
      5.4.4. Example 20—Enrichment of Reaction Product from Enzymatic Resolution of trans-3-(4-Methoxyphenyl)glycidic Acid Methyl Ester Using Sodium Bisulfite
      5.4.5. Example 21—Recovery of trans-3-(4-Methoxyphenyl)glycidic Acid Methyl Ester from Tolune Using Concentrated Sodium Bisulfite
      5.4.6. Example 22—Degree of Inhibition on Representative Enzymes of Reaction Products
      5.4.7. Example 23—Resolution of trans-3-(4-Methoxyphenyl)glycidic Acid Methyl Ester Using Sodium Bisulfite
      5.4.8. Example 24—Resolution of trans-3-(4-Methoxyphenyl)glycidic Acid Methyl Ester in the Absence of Sodium Bisulfite
      5.4.9. Example 25—Resolution of trans-3-(4-Methoxyphenyl)glycidic Acid Methyl Ester Using Sodium Bisulfite and Extended Reaction Time
      5.4.10. Example 26—Resolution of trans-3-(4-Methoxyphenyl)glycidic Acid Methyl Ester Using Sodium Bisulfite in a Larger Scale
      5.4.11. Example 27—Resolution of trans-3-(4-Methoxyphenyl)glycidic Acid Methyl Ester in a Multiphase Enzyme Membrane Reactor Using Palatase M
      5.4.12. Example 28—Batch Reactions in Toluene Followed by Direct Crystallization of trans-3-(4-methoxyphenyl glycidic Acid Ester (GLOP) Therefrom
      5.4.13. Example 29—Bench-Scale Dispersed Phase Enzymatic Resolution Providing High Optical Purity Solutions
      5.4.14. Example 30—Large-Scale Membrane Reactor Process Providing Organic Solutions of Highly Resolved GLOP
      5.4.15. Stability of GLOP in Some Representative Types of Solvents
   5.5. Further Considerations with Regard to Choice of Solvent
      5.5.1. The Effect of Solvent on Enzyme Activity
      5.5.2. Determination of the Non-Enzymatic Degradation of Substrate Ester
   5.6. Post-Enzyme Resolution Clean-Up of Crude Reaction Products by Extraction with a Carbonyl Adduct-Forming Agent
      5.6.1. Example 34—Purification of Crude Organic Solution by Extraction with Aqueous Bisulfite Anion
   5.7. Reactivity of the Oxirane Ring

1. INTRODUCTION

The esters of trans-3-(4-methoxyphenyl)glycidic acid have utility as precursors in the chemical synthesis of diltiazem. Moreover, these compounds present a very attractive point in the overall synthetic route to diltiazem at which to introduce the desired stereochemistry into the diltiazem precursors through resolution of the racemic glycidic esters and use of the correct, optically purified precursor ester. The present invention pertains to a novel enzymatic method for resolving a racemic mixture of esters of the (2R,3S)- and (2S,3R)-enantiomers of trans-3-(4-methoxyphenyl)glycidic acid. It also pertains to a process for diltiazem production incorporating this resolution step and to membrane reactor means for improving the efficiency of enzymatic resolution of this diltiazem intermediate. The amelioration of the effects of an inhibitory aldehyde by-product of the reaction process by means of its formation of an adduct with an agent provided in the aqueous reaction phase is also an aspect of the present invention. Moreover, selected organic solutions of the optically active glycidic ester intermediates have been developed which are particularly useful in subsequent processes involving the isolation of the intermediate directly from the solution or use of the solution to introduce a new reagent for a further chemical transformation.

2. BACKGROUND OF THE INVENTION

2.1. Diltiazem and its Analogues

Diltiazem, the chemical structure of which is shown in FIG. 1, is an optically active pharmaceutical compound. More specifically, diltiazem, the chemical name of which is (+)-5-[2-(dimethylamino)ethyl]-cis-2,3-dihydro-3-hydroxy-2-(p-methoxyphenyl)-1,5-benzothiazapin-4(5)-one acetate (ester), consists of a substituted benzothiazapene wherein both chiral carbon atoms have the S absolute stereoconfiguration (H. Inoue et al., U.S. Pat. No. 3,562,257). Diltiazem has proven useful for the treatment of angina due to coronary artery spasm, and for exertional angina. The beneficial therapeutic effects achieved with diltiazem are believed to be derived from the inhibition of calcium ion influx during depolarization of the cell membrane in both cardiac and smooth muscle. Diltiazem is known to prevent coronary artery spasm, both spontaneous and ergonovine provoked, and to decrease peripheral vascular resistance. Diltiazem is marketed by Tanabe and by Marion Laboratories in the United States, where it is sold under the tradename Cardizem®. Analogues to diltiazem are also known to exist, e.g., wherein the benzothiazapene moiety has a single chlorine substituent on the aromatic ring.

Figure 2:
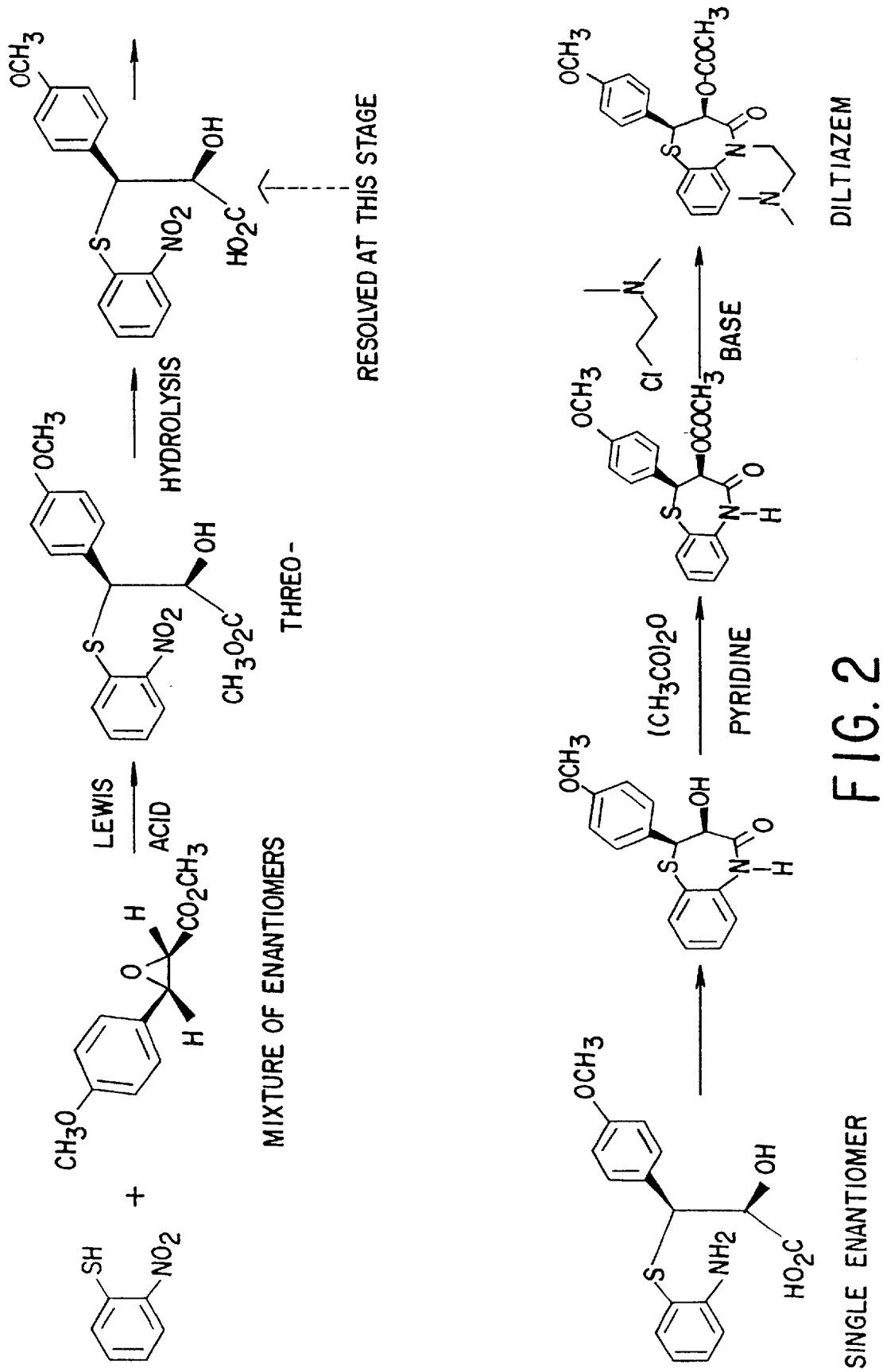

Diltiazem is currently being manufactured via a process similar to that shown in FIG. 2. The first step in the synthetic sequence involves the Lewis acid-catalyzed nucleophilic attack of o-nitrothiophenol on methyl trans-3-(4-methoxyphenyl)glycidate, as a mixture of enantiomers, to give the threo compound shown (H. Inoue et al., *J. Chem. Soc. Perkin Trans. I*, 1984, 1725; H. Inoue et al., *J. Chem. Soc. Perkin Trans. I*, 1985, 421; H. Inoue et al., U.S. Pat. No. 4,420,628). This threo compound then needs to be resolved at a subsequent step in the synthetic pathway in order to arrive at the optically active final product (diltiazem).

Alternative production routes to diltiazem utilize o-aminothiophenol in place of o-nitrothiophenol in the step involving opening of and addition to the oxirane ring (S. Nagao et al., U.S. Pat. No. 4,416,819). Such alternative processes also utilize methyl trans-3-(4-methoxyphenyl)-glycidate as an intermediate, and thus are subject to improvement by the process of the present invention.

2.2. The Stereochemistry of Diltiazem and its Precursors

It is known that the above pharmacological effects reside in only one of the two enantiomers of the diltiazem, namely, the d-enantiomer (Merck Index, 10th Edition, 1986, p. 466; Physician's Desk Reference, 41st Edition, 1987, p. 1173). Thus, there is a need to produce diltiazem with the correct stereochemistry, and to introduce such correct stereochemistry at an efficient point in the overall synthesis by production of an optically purified and stereochemically correct intermediate or precursor. As discussed above, diltiazem can be produced from a 3-(4-methoxyphenyl)glycidic acid ester intermediate. At the present time, this intermediate is used in its racemic form, i.e., it is not optically active.

Figure 3:
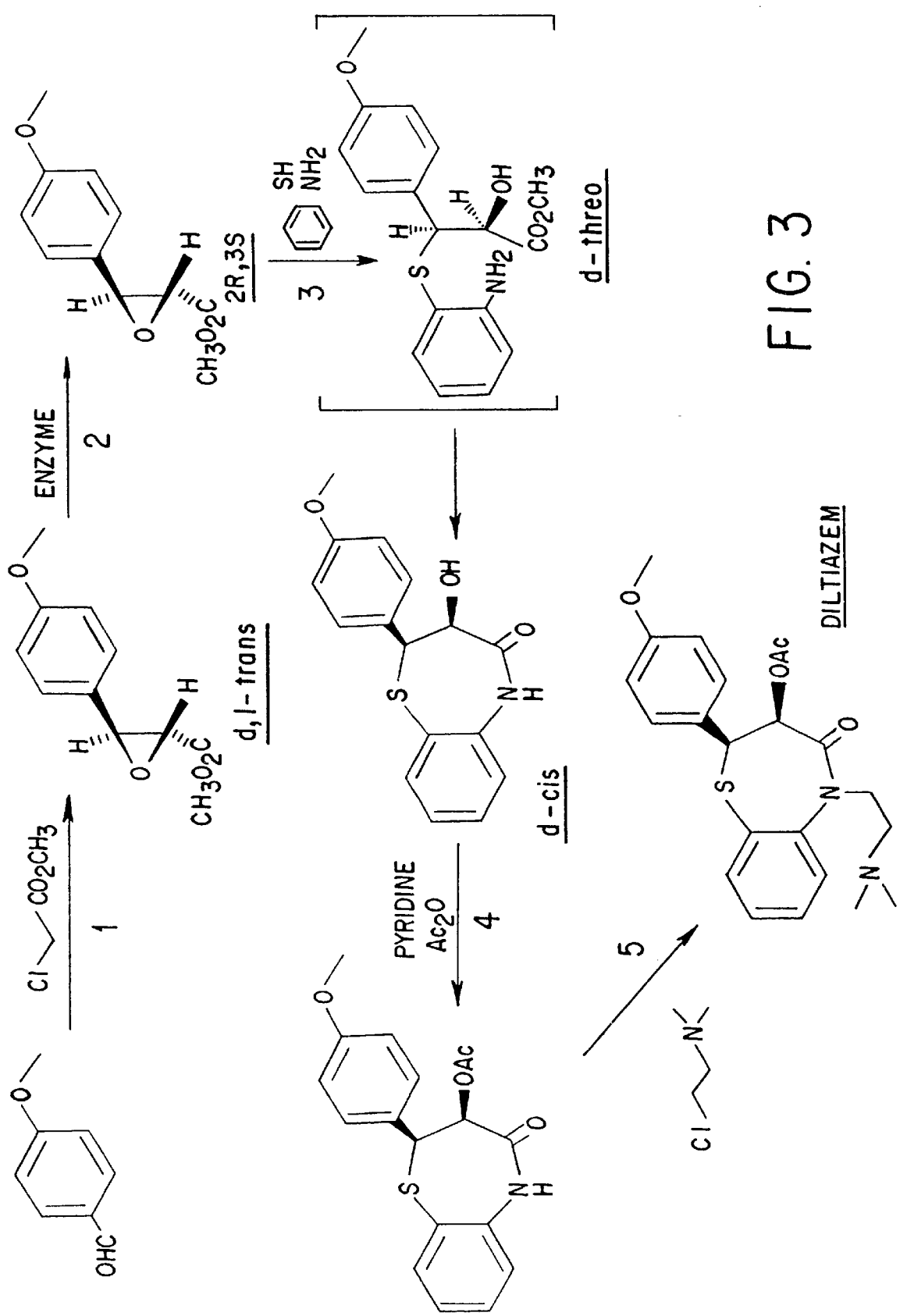

The 3-(4-methoxyphenyl)glycidic acid ester, shown in FIG. 3, contains two chiral centers at carbon atoms 2 and 3, both of which may assume either the R or S absolute configurations. Generally speaking, molecules containing n chiral centers and having no elements of reflective symmetry, will have $2^n$ stereoisomers. In a molecule with 2 chiral centers, there will thus be $2^2$ or 4 stereoisomers. Furthermore, in the case of a molecule having only two chiral centers, these four stereoisomers will be related as a diastereomeric pair of enantiomers, that is two diastereomers each existing as a mixture of its two enantiomers. In the specific case of 3-(4-methoxyphenyl)glycidic acid esters, the two diastereomeric forms are described as cis and trans isomers. The cis isomer is defined as the diastereomer in which the two hydrogen atoms bonded to the carbon atoms of the oxirane ring, that is carbon atoms 2 and 3, eclipse each other, that is, are on the same side of the plane defined by the oxirane ring substructure of the molecule. The trans isomer is defined as the diastereomer in which the hydrogen atoms bonded to carbon atoms 2 and 3 lie on opposite sides of the plane of the oxirane ring. Thus the relative configurations of carbon atoms 2 and 3 are fixed in each diastereomer, although each diastereomer will still exist as a pair of enantiomers. Because diastereomeric compounds are physically distinct entities, not related by symmetry operations performed on the entire molecule, they are physically distinguishable and may be produced separately by the appropriate conventional chemical methods.

The thermodynamically favorable trans diastereomer of a given 3-(4-methoxyphenyl)glycidic acid ester can be synthesized via the Darzen's glycidic ester condensation, and rendered free of any cis diastereomer by conventional purification methods. The trans diastereomer exists in two enantiomeric forms, one having absolute configuration R at carbon atom 2, and absolute configuration S at carbon atom 3. This enantiomer is described as the (2R,3S) isomer. The other enantiomer of the trans diastereomer will have absolute configuration (2S,3R). The enantiomers of the cis diastereomer exhibit absolute configurations (2S,3S) and (2R, 3R). The particular glycidic ester enantiomer having absolute configuration (2R,3S) is the compound desired as an optically purified synthetic precursor to diltiazem.

2.3. Techniques for Resolution of Glycidate Esters

The production of (2R,3S)-3-(4-methoxyphenyl)glycidic acid methyl ester has previously been achieved through two fundamentally different procedures. The first procedure involves the synthesis of the chiral glycidic acid methyl ester from achiral precursors, with the creation of chirality during a specific reaction which utilizes a chiral oxidation reagent. Thus, trans-cinnamyl alcohol is asymmetrically epoxidized to give the desired oxirane ring structure, with the correct stereochemistry being created at carbon atoms 2 and 3 simultaneously (K. Igarashi et al., U.S. Pat No. 4,552,695).

The second procedure, which is generally considered more classical, involves the use of an optically pure reagent used in stoichiometric quantities, to form diastereomeric adducts with the enantiomers of racemic esters or salts of trans-3-(4-methoxyphenyl)glycidic acid (M. Hayashi et al., Japan 5 Kokai Tokkyo Koho J P 61/145160 A2 [86/145160] (1986); M. Hayashi et al., Japan Kokai Tokkyo Koho J P 61/145160 A2 [86/145160] (1986)). These adducts are physically distinguishable, and may be separated by conventional procedures such as fractional crystallization. The thus separated adducts are then decomposed under controlled conditions to leave the separated enantiomers, and the recovered resolving reagent.

Both of these procedures suffer drawbacks, however. In particular, the first procedure involves the use of an unusual catalyst, namely, dialkyl tartrate titanium(IV) isopropoxide, which requires anhydrous conditions and concomitant handling procedures (K. B. Sharpless et al., *J. Amer. Chem. Soc.*, 1980, 102, 5974; K. B. Sharpless et al., *Pure Appl. Chem.*, 1983, 55, 589). More importantly, the reaction which creates the desired stereochemistry does not produce the methyl ester directly. Two further reactions are required beyond the point at which chirality is introduced, involving the production (by oxidation of the alcohol) and esterification of the glycidic acid itself, which is an unstable compound requiring special handling. The second procedure suffers from the need for stoichiometric quantities of previously resolved chiral materials or resolving agents such as alpha-methylbenzylamine (S. Nagao et al., U.S. Pat. No. 4,416,819). Because of the expense of such resolving agents, there also exists a need to recover these materials in a quantitative manner after the resolution step. Additionally, the energy and solvent requirements of large-scale crystallization processes make them unattractive.

2.4. Enzymatic Resolution of Racemic Mixtures

Another approach to the resolution of racemic mixtures of chiral compounds involves subjecting racemic compounds to the enantioselective action of various enzymes. Enzymatic resolution has been widely employed for the lab-scale, preparative-scale, and industrial-scale production of many optically pure compounds including esters but not heretofore the glycidate esters.

Many different classes of enzymes have been used for the resolution of stereoisomers on a preparative scale, including hydrolases (especially the lipases, proteases and esterases such as chymotrypsin), lyases and oxidoreductases (e.g., amino acid oxidases and alcohol reductases). Generally speaking, enzymes for use in resolutions should ideally exhibit broad substrate specificity, so that they will be capable of catalyzing reactions of a wide range of "unnatural" substrates, and they should exhibit a high degree of stereoselectivity for catalyzing the reaction of one isomer to the exclusion of others.

The hydrolases (e.g., lipases, proteases and esterases) are among the more attractive enzymes for use in resolutions, because they are commercially available at reasonable cost, they do not require expensive cofactors, and some of them exhibit reasonable tolerance to organic solvents. Additionally, chiral chemistry often involves alcohols, carboxylic acids, esters, amides and amines with chiral carbons, and carboxyl hydrolases are preferred choices as stereoselective catalysts for reactions of such species (Cambou, B. and A. M. Klibanov, *Biotechnol. Bioeng.*, 1984, 26, 1449). Many pharmaceuticals and their intermediates exhibit very low solubilities in water, and accordingly a number of enzyme-mediated optical resolutions have been conducted under multiphasic reaction conditions.

Enzymatic treatment has been applied to the resolution of racemic mixtures of amino acid esters. For example, Stauffer (U.S. Pat. No. 3,963,573) produced optically pure N-acyl-L-methionine by treating N-acyl-D,L-methionine ester with microbial proteases and separating the product acid from the reaction mixture. Similarly, Bauer (U.S. Pat. No. 4,262,092) prepared optically pure D-phenylalanine ester by subjecting a racemic mixture of an N-acyl-D,L-phenyl-alanine ester to the action of a serine protease, separating the unaffected N-acyl-D-phenylalanine ester, and removing the N-acyl and ester groups. Matta et al. (i J. Org. Chem., 1974, 39, 2291) used chymotrypsin in the resolution of precursors of the drug 3-(3,4-dihydroxyphenyl)alanine or dopa.

Enzymes have also been explored for the resolution of other compounds such as agricultural chemicals, sometimes in biphasic reactions systems. In particular, Cambou and Klibanov (*Biotech. Bioeng.*, 1984, 26, 1449) examined the use of lipase immobilized in porous beads for the enzymatic resolution of mixtures of (R,S)-2-(p-chloro-phenoxy) propanoic acid (whose R isomer is a herbicide) and various esters thereof. The differing solubility properties of the acids and esters used in their studies required the dispersion and agitation of mixtures containing the immobilized solid-phase enzyme, an aqueous buffer, and the water-immiscible organic phase containing solvent and reactant—a relatively inefficient process.

Additional examples can be provided of the state-of-the-art of enzyme-mediated resolution as applied to the production of optically purified pharmaceuticals, albeit not to the enzymatic resolution of diltiazem precursors. Sih (U.S. Pat. No. 4,584,270) has disclosed enzymatic means for the production of optically pure (R)-4-amino-3-hydroxy-butanoic acid, a key intermediate in the preparation of L-carnitine. Additionally, certain optically pure D-amino acids (in particular, the D-arylglycines such as phenylglycine and 4-hydroxyphenylglycine) are used as side chains in the manufacture of semisynthetic penicillins and cephalosporins. Schutt et al. (*Biotechnol. Bioeng.*, 1985, 27, 420) have subjected racemic mixtures of such nonpolar N-acyl-D,L-amino acid esters to the hydrolytic action of subtilisin in two-phase systems for the purpose of obtaining optically purified D-amino acids. In still other references, enzymes derived from microorganisms were utilized to resolve esters of naproxen and ibuprofen. C. J. Sih et al. (*Tetrahedron Letters*, 1986, 27, 1763) describes that esters of ibuprofen and naproxen are capable of being stereospecifically resolved using a microorganism-derived lipase.

In summary, there exists a need in the art for more efficient methods for production of optically purified diltiazem and its analogues, and in particular for improved processes for the optical resolution of racemic diltiazem precursors including the esters of trans-3-(4-methoxyphenyl) glycidic acid. Furthermore, while enzymatic resolution techniques have been employed for the production of many optically pure pharmaceuticals and their precursors, this technique has not yet been disclosed and successfully applied to the resolution of the glycidate esters that are chiral intermediates in the production of diltiazem. The present invention provides such an enzymatic resolution method.

3. SUMMARY OF THE INVENTION

The resolution process of the present invention is accomplished through the use of an enzyme that preferentially catalyzes hydrolysis of one of the two enantiomers of a given glycidic ester to the parent glycidic acid, leaving intact the enantiomer having the desired absolute configuration as the glycidic ester. A specific embodiment of this invention pertains to hydrolytic enzymes, with particularly preferred enzymes being chosen from the lipases and proteases, capable of preferentially hydrolyzing simple alkyl esters (e.g., the methyl ester) of (2S,3R)-methoxyphenylglycidate at a rate higher than the rate of hydrolysis of the corresponding (2R,3S)-enantiomer of methyl methoxyphenylglycidate, permitting recovery of the latter species in optically purified form for use as an optically resolved intermediate in the production of diltiazem.

Also included in this invention and described herein are methods for the efficient conduct of the enzymatic resolution step, including the use of multiphase and extractive membrane reactors to improve the efficiency of the biocatalytic reaction, as well as the provision of bisulfite anion in the aqueous reaction phase for the purpose of forming an adduct with an otherwise inhibitory and troublesome aldehyde by-product.

The present invention provides a method for obtaining an organic solution comprising an optically active diastereomer of a glycidic acid ester which involves preparing an organic solution comprising the diastereomer in a water-immiscible organic solvent, which diastereomer may be present as a mixture of enantiomers. This solution is then brought into contact with an aqueous mixture comprising water and an enzyme which catalyzes the enantioselective hydrolysis of the undesired glycidyl ester, thus enriching the organic solution in the desired enantiomer. The product enantiomer may then be crystallized directly from the enriched solution or may then be employed, while in this same solution, in a subsequent reaction.

4. BRIEF DESCRIPTION OF THE FIGURES

This invention may be more readily understood by reference to the following detailed description of the invention and figures:

FIG. 1. is a representation of the chemical structure of the diltiazem molecule.

FIG. 2. is a schematic representation of a prior-art process for the production of diltiazem.

FIG. 3. is a schematic representation of a method for the production of the pharmaceutically active diltiazem stereoisomer based on the use of the optically purified precursor (2R,3S)-3-(4-methoxyphenyl)glycidate methyl ester, said precursor being resolved from the racemic d,l-trans mixture in step 2 of the diagrammed process.

FIG. 4. is a representation of the chemical structures of trans- and cis-isomers of the 3-(4-methoxyphenyl)glycidic acid ester, wherein it is the (2R,3S)-trans stereoisomer which is particularly preferred for diltiazem manufacture and wherein R denotes the esterified alcohol moiety.

For purposes of clarity, specific stereoisomers with particular absolute configurations about the chiral carbons, and generally the preferred configuration for diltiazem production, are shown in the above figures. However, it should be noted that current prior-art diltiazem processes such as that shown in FIG. 2 utilize racemic intermediates (e.g., the methyl ester of d,l-trans-3-(4-methoxyphenyl)-glycidic acid in the initial steps of the process.

FIG. 5. is a schematic representation of the enzymatic resolution step of the present invention, wherein the two-component racemic mixture of d,l-trans enantiomers of an ester of 3-(4-methoxyphenyl)glycidic acid is subjected to the action of a stereoselective enzyme with the result that the undesired (2S,3R)-enantiomer is preferentially hydrolyzed to the corresponding enantiomer of its parent acid, leaving intact the enantiomer with the desired (2R,3S) absolute configuration in the chemical form of the unreacted ester.

Figure 6:
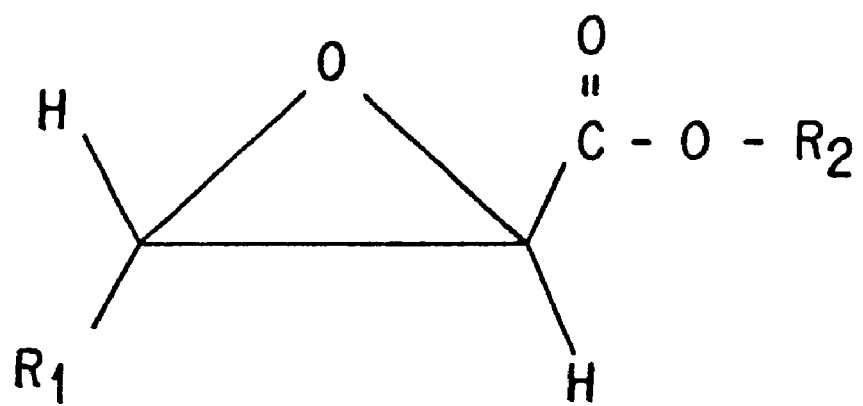

FIG. 6. is a schematic representation of a substituted glycidate ester that is susceptible to enzymatic resolution by the process of the present invention.

Figure 7:
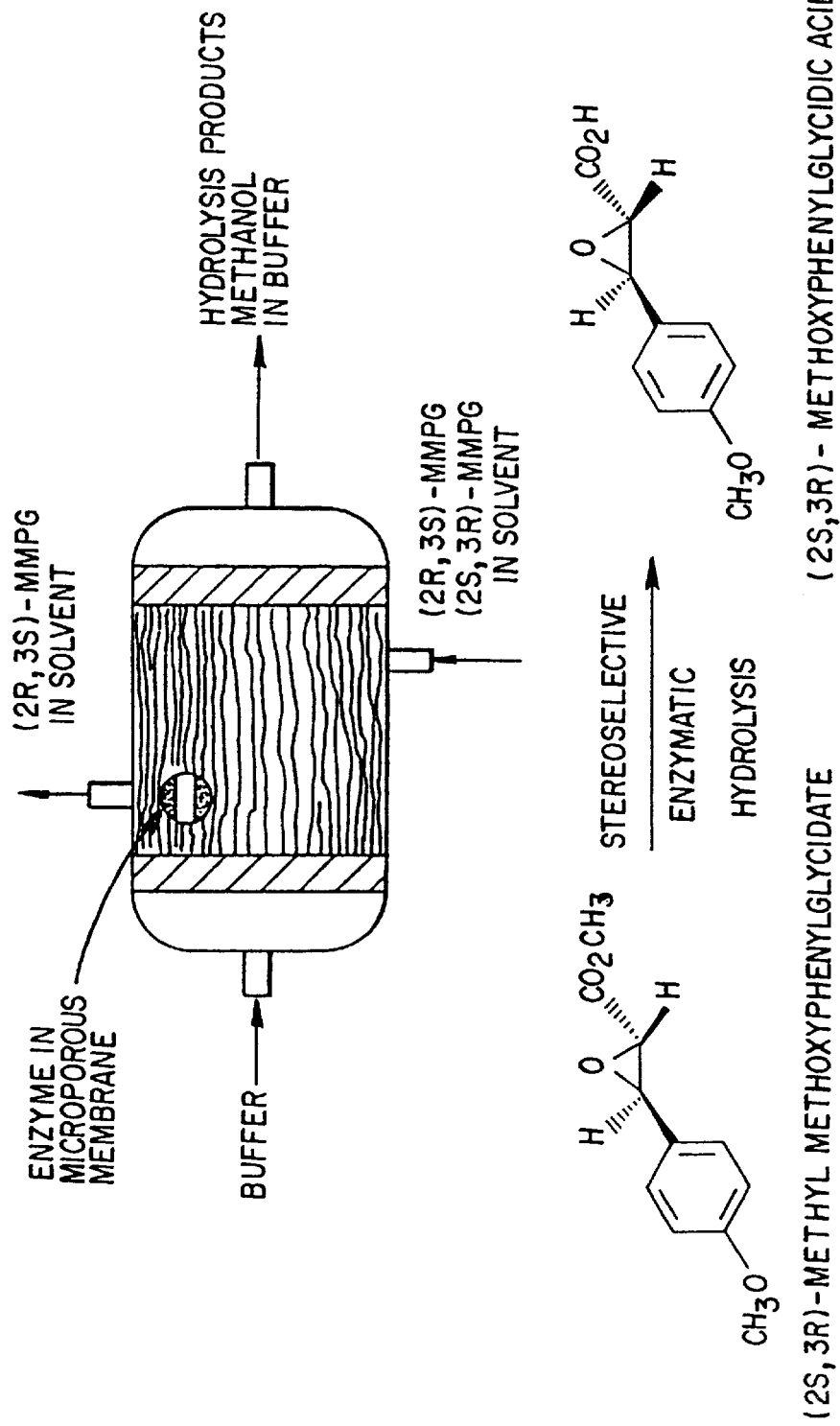

FIG. 7. is a schematic representation of a hollow-fiber multiphase/extractive enzyme membrane reactor with organic-phase feed of the racemic methyl 3-(4-methoxyphenyl)-glycidate esters (MMPG), aqueous-phase withdrawal of water-soluble enzymatic reaction products including the (2S,3R)-3-(4-methoxyphenyl)glycidate salt and its decomposition products, and organic-phase withdrawal of the unreacted and desired (2R,3S)-3-(4-methoxyphenyl)glycidate methyl ester.

Figure 8:
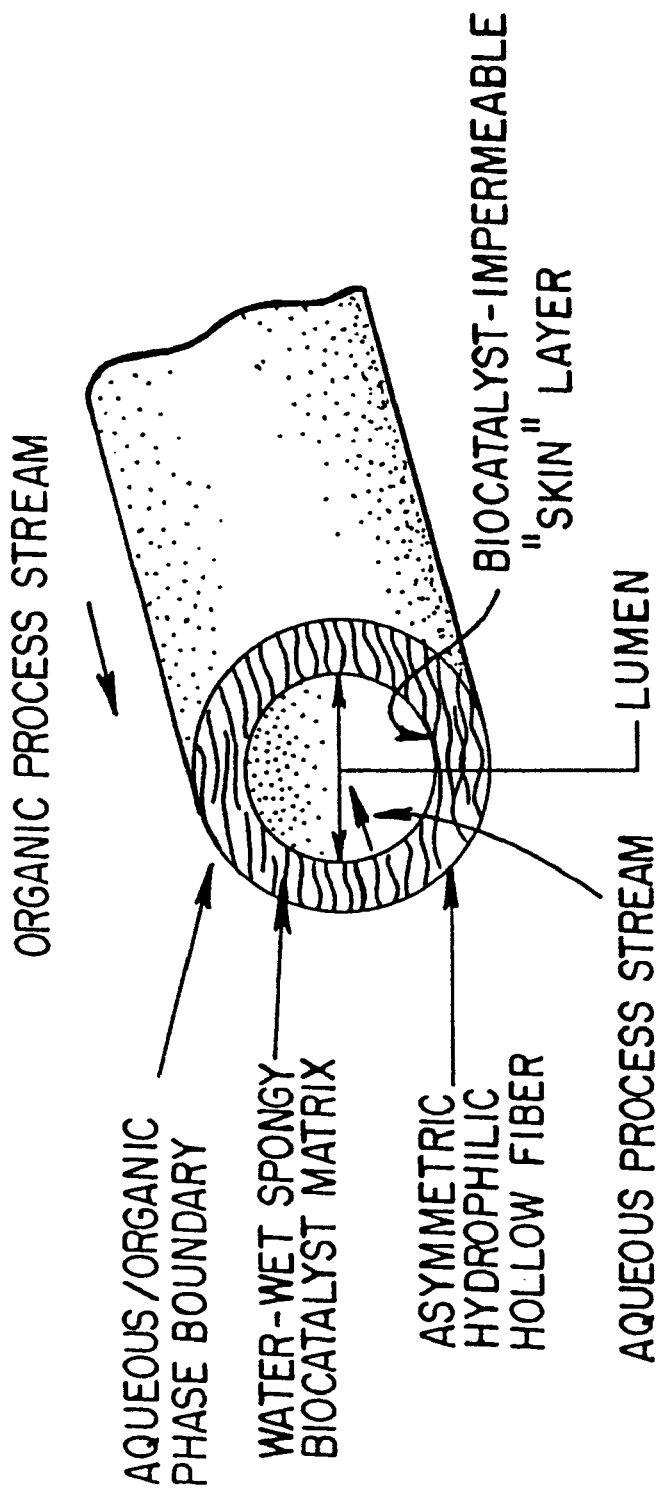

FIG. 8. is a schematic representation of a preferred embodiment of the invention wherein the enzyme is reversibly contained within an asymmetric, hydrophilic, and microporous hollow-fiber membrane.

Figure 9:
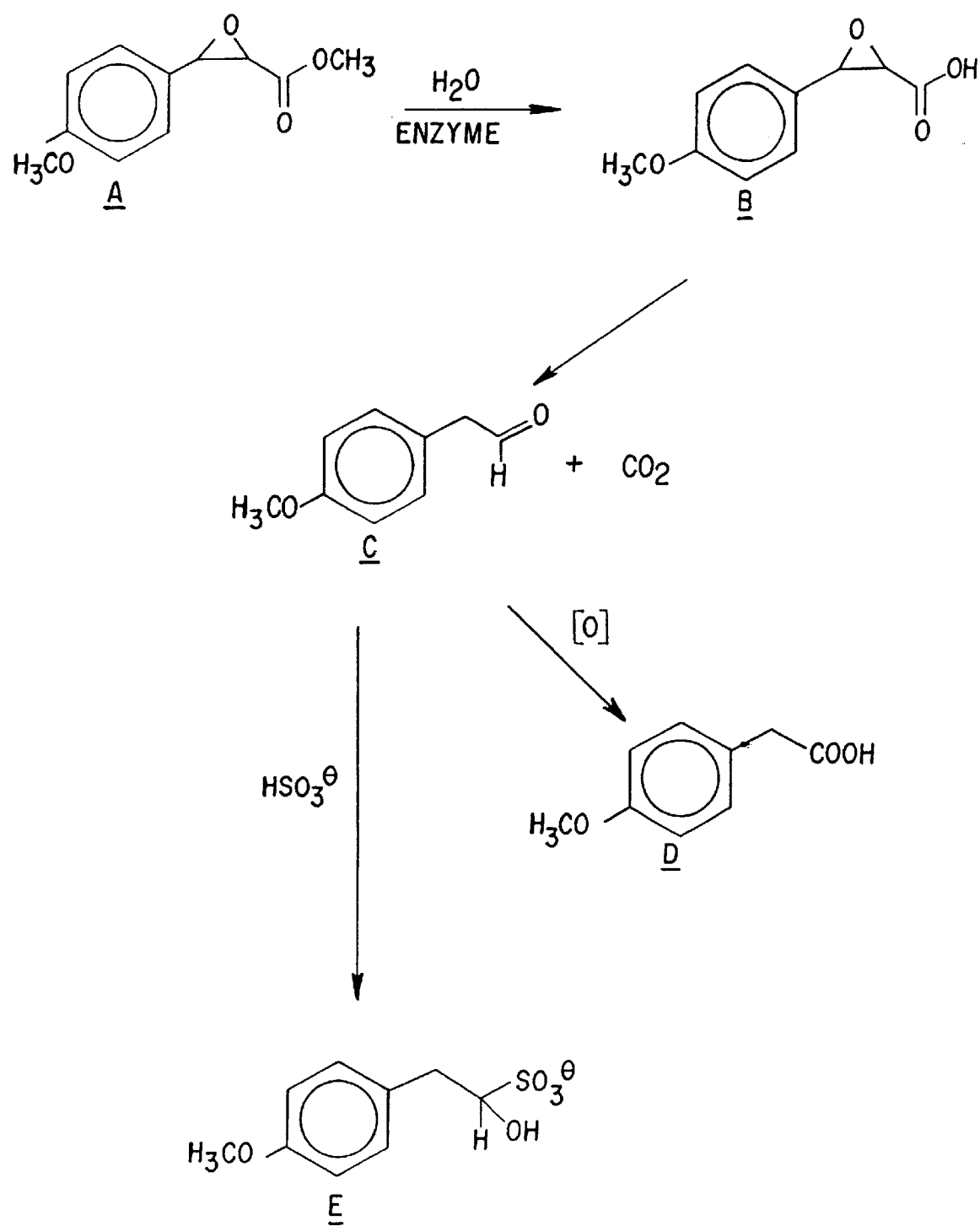

FIG. 9. is a diagram summarizing the chemistry involved in the formation of an aldehyde by-product from its glycidic acid precursor, as well as the chemistry of two subsequent reactions of the aldehyde—namely, adduct formation with bisulfite anion and oxidation.

Figure 10:
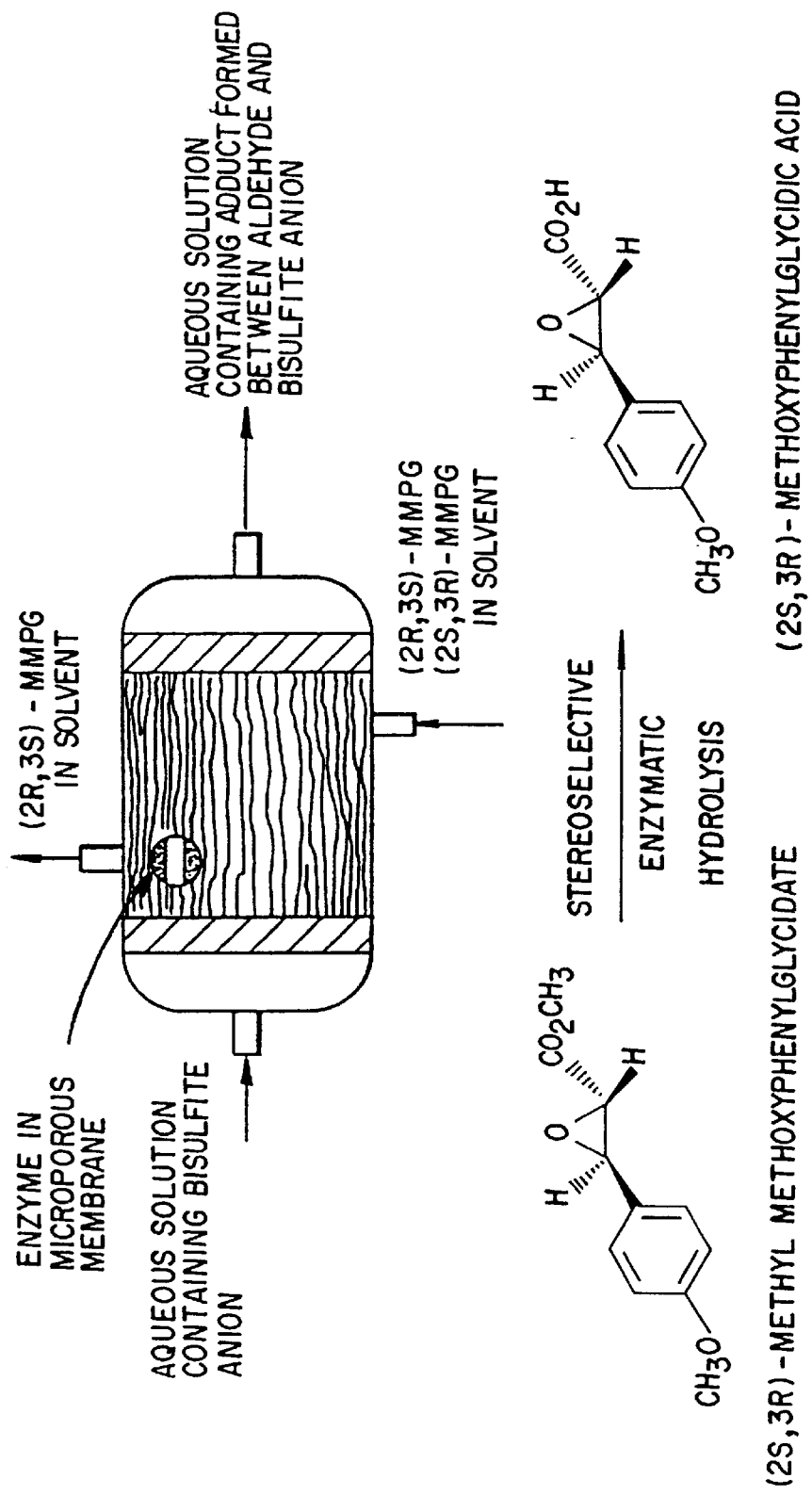

FIG. 10. is a schematic representation of a hollow-fiber multiphase/extractive enzyme membrane reactor supplied with a racemic feed mixture of methyl 3-(4-methoxyphenyl)glycidate esters (MMPG) in a water-immiscible organic solvent on one side of the membrane and an aqueous solution containing bisulfite anion supplied to the opposite side of the membrane. Water-soluble reaction products—notably including the adduct formed by reaction of bisulfite with the inhibitory aldehyde by-product—are shown being withdrawn via the exiting aqueous process stream, while the unreacted and desired (2R-3S)-3-(4-methoxyphenyl) glycidate methyl ester is withdrawn via the exiting organic process stream.

5. DETAILED DESCRIPTION OF THE INVENTION

It is an object of the present invention to provide an improved process for the production of resolved glycidic esters, subsequently useful in the synthesis of optically pure diltiazem. Specifically, this invention relates to production of optically pure intermediates, namely (2R,3S)-3-(4-methoxyphenyl)glycidic acid methyl ester and other simple alkyl esters, by enzymatic resolution of a racemic mixture of the d,l-trans esters. This is accomplished in a subtractive resolution process, wherein the undesired (2S,3R)-glycidate ester is enzymatically hydrolyzed and removed from the desired (2R,3S)-enantiomer, with the net result that the latter compound is optically purified in the process.

In a process for diltiazem manufacture, the resolution of threo-2-hydroxy-3-(4-methoxyphenyl)-3-(2-nitrophenyl-thio)propionic acid methyl ester can be avoided if the glycidic acid ester subject to the initial nucleophilic attack by o-nitrothiophenyl to produce the threo-compound is, itself, optically purified. The enzymatic resolution process of this invention provides means by which to accomplish the enantioselective preparation of the desired optically active intermediate, i.e. a trans-(2R,3S)-3-(4-methoxyphenyl) glycidic acid ester.

It is known that glycidic acids are unstable except under certain conditions; however, the esters of glycidic acids are relatively stable (apart from their hydrolytic instability) and are useful synthetic intermediates. In order to use a glycidic acid ester as a synthetic precursor in the synthesis of diltiazem, and to produce the desired stereochemistry in the final product, the glycidic acid ester with absolute configuration (2R,3S) is required. Thus, a suitable combination of enzyme and glycidic acid ester is required that results in the enzyme-catalyzed hydrolysis of the enantiomer with (2S, 3R) absolute configuration, permitting recovery of the enantiomer with absolute configuration (2R,3S) as the unhydrolyzed glycidic ester.

5.1. Multiphased Enzymatic Reaction Processes

The present process for the resolution of glycidic esters is one in which the undesired enantiomer present in the racemic glycidic ester substrate is selectively transformed by hydrolysis of the ester function into a species easily separated from the remaining glycidic ester enantiomer by known physical methods. Specifically, in the case of this invention, the desired ester enantiomer is soluble in organic solvents that are immiscible with water, while at least one of the products of hydrolysis of the undesired glycidic ester has appreciable water solubility. (As the term "immiscible" is used herein, it is meant to encompass solvents which are completely, substantially, or partially immiscible with water—i.e., solvents that form a separate organic phase when placed in contact with water.) The resolution process described herein is a kinetic resolution process in which each enantiomer of the racemic substrate mixture exhibits some susceptibility to enzymatic hydrolysis, but one of said enantiomers is hydrolyzed more rapidly than the other in the presence of an appropriate enzyme catalyst. In this situation, the ability of an enzyme to discriminate between two competitively reacting enantiomers may be quantified by the enantioselectivity value E, as described by C.-S. Chen et al. (*J. Am. Chem. Soc.*, 1982, 104, 7294). The formula for calculation of E in the case of a subtractive kinetic resolution process is given as follows:

$$E=\{\ln[(1-x)(1-ee(S))]/\ln[(1-x)(1+ee(S))]\}$$

where x is the degree of conversion of the entire quantity of starting substrate, expressed as a decimal fraction, and ee(S) is the enantiomeric excess of the remaining, non-hydrolyzed substrate enantiomer, also expressed as a decimal fraction. This formula permits comparison of enzyme reactions which have proceeded to different degrees of conversion, in which case direct comparison of the enantiomeric excess of remaining glycidic ester substrate is not possible. It is also possible to use this E value and corresponding calculations to compare the apparent selectivity of the same enzyme operating under varying conditions (see, Section 5.5.1).

Despite the known inactivating effects of epoxides on enzymes, it is possible as taught by this invention to use enzymes to catalyze the hydrolysis of carboxylic acid esters of the epoxide containing compounds generally known as glycidic acids, in an enantioselective manner. The racemic carboxylic acid esters of the parent glycidic acids include those having the general structure shown in FIG. 6, wherein $R_1$ is a substituent selected from the group of phenyl and substituted phenyl, and $R_2$ is a group derived from an alcohol. The substituted phenyl group may be substituted with various groups including hydroxy, methoxy, phenoxy, benzyloxy, alkoxy, aryloxy, arylalkoxy, and halide. A particularly important $R_1$ group is 4-methoxyphenyl, since it is this group which is pertinent to diltiazem manufacture. The phenyl group substituent may occupy one or more of the ortho, meta, or para positions with respect to the glycidic ester moiety. With regard to the alcohol moiety $R_2$, this group will be selected from the group consisting of straight-chain alkyl with 1 to 8 carbon atoms, branched-chain alkyl with 3 to 8 carbon atoms, substituted alkyl, aryl, substituted aryl, and alkoxyalkyl. Preferred alkyl substituents include methyl, ethyl, isopropyl, and isobutyl, while preferred alkoxyalkyl substituents include the methoxyethyl and ethoxyethyl groups.

The preferred embodiment of this invention corresponds to the case in which $R_1$ is a para-methoxyphenyl group, $R_2$ is a methyl group, the relative configuration of groups $R_1$ and $R_2$ are trans, and the absolute configuration of the desired glycidic acid ester product after enzymatic resolution is (2R,3S). It should be noted that the corresponding cis glycidic ester diastereomer, in which groups $R_1$ and $R_2$ are on the same side of the plane of the epoxide ring, may also be resolved, and the resulting (2R,3R)-cis-3-(4-methoxyphenyl)glycidic acid esters may also be used in the subsequent production of diltiazem.

In the present invention, enzyme catalysts are present either dissolved or dispersed in an aqueous phase. Although the glycidic esters described herein are generally quite insoluble in water, the epoxide ring is susceptible to opening through nucleophilic attack by species such as hydroxide ions and water molecules, even in the absence of enzymes. Exposure of the preferred substrate of this invention, described above, to an aqueous sodium phosphate buffer solution of pH 7.0 for 18 hours at ambient temperature, in the absence of any organic solvent or enzyme preparation, leads to the loss of glycidic ester, and the formation of a water-soluble compound. However, in the presence of toluene in a 1-to-1 phase ratio with the same aqueous phase, there was no loss of glycidic ester over the same period of time, and 100% of the glycidic ester could be recovered by separation and evaporation of the organic phase. Therefore, the use of an organic phase as a method for protecting the substrate from undesired transformations by water, hydroxide ions, or water-soluble buffer systems is a significant aspect of this invention. These experimental observations indicate the need for a biphasic system, and preferably a multiphase/extractive membrane reactor as described below, for efficiently conducting the enzyme-mediated resolution process disclosed herein.

In the present invention, a wide variety of commercially and otherwise available preparations of hydrolytic enzymes can be used directly to perform enantioselective hydrolyses on the glycidic esters represented by the structure in FIG. 6. The enzymes contained in such preparations may be from any of the general classes of hydrolytic enzymes described as esterases, lipases, proteases, peptidases, and acylases. In addition, such preparations may be derived from both eukaryotic and prokaryotic cells, including but not limited to those from the following mammalian sources; porcine liver, porcine pancreas, porcine kidney, and bovine pancreas; the plant source wheat germ; and those from the following microbial genera: Aspergillus, Candida, Geotrichum, Humicola, Mucor, Penicillium, Rhizopus, Streptomyces, Bacillus, Chromobacterium, and Pseudomonas. In preferred embodiments of this invention, commercial preparations containing lipases derived from the microorganisms *Mucor javanicus, Mucor miehei,* and other Mucor species, *Candida cylindracea, Pseudomonas fluorescens,* and commercial preparations containing the protease known as Protease BPN' from *Bacillus sp.,* are used as hydrolytic catalysts.

Reaction conditions for the enzymatic hydrolysis include the use of a two-phase system, in which the enzyme preparation is dissolved or dispersed in an aqueous phase, and the glycidic ester is dissolved in an organic phase chosen from organic solvents known to be appreciably immiscible with water. The pH of the aqueous phase may range from 5 to 9, according to the pH optimum of the enzyme preparation in use, and provided that the pH chosen does not have a deleterious effect on the glycidic ester. It is desirable to maintain the pH of the aqueous phase within the desired range over the course of the hydrolysis by the use of a buffer system, or an automatic titrator or other pH controlling device. Similarly, the temperature at which the hydrolysis is performed may vary over a wide range, provided that both the aqueous and organic phases remain liquid, the enzyme chosen does not experience denaturation at a rate too rapid to allow its use, and the glycidic ester remains stable. The relative volumes of the aqueous and organic phases are not critical, and may vary over a wide range. Likewise, the concentration of enzyme preparation in the aqueous phase, the concentration of glycidic ester in the organic phase, and the ratio of these concentrations, are not critical and may vary over a wide range. In the preferred embodiment of this invention, the ratio of the organic to aqueous phase, the temperature, the pH of the aqueous phase, and the concentrations of the enzyme preparation in the aqueous phase and the glycidic ester in the organic phase, are chosen to be such that an optimal combination of rate and enantioselectivity of hydrolysis is realized.

Since the racemic glycidic ester substrate is soluble in the organic phase and nearly insoluble in the aqueous phase, the enantiomer of the racemic substrate mixture which is less easily hydrolyzed will be present in the organic phase in a higher concentration than that of the more readily hydrolyzed glycidic ester enantiomer, thus creating an organic solution of the desired glycidic ester enantiomer which increases in the degree of resolution (i.e., enantiomeric excess) as a function of the extent of hydrolysis and the enantioselectivity value E. The extent of hydrolysis of the total racemic glycidic ester substrate may be adjusted to permit the recovery of the desired glycidic ester at any desired level of enantiomeric excess; higher conversions yield organic-phase product esters of increasing optical purity.

In the case of the subtractive resolution process of the present invention, the optimum situation is that in which an enzyme displays an infinitely large E value. In this case, at 50% hydrolysis of the total starting substrate, 100% of the non-hydrolyzed material will remain in the organic phase after reaction at an optical purity of 100% enantiomeric excess. However, if a given enzyme displays a lower E value, the overall extent of hydrolysis must be allowed to proceed past 50%, to an extent that is determined by the formula derived by Chen et al. and reproduced above. Preferably, the enzyme catalyst will be chosen to display the largest E value possible, thus permitting the recovery of the greatest amount of desired glycidic ester enantiomer for a given degree of enantiomeric excess. This material may then be recovered by removing the organic solvent by known methods.

A preferred enzymatic resolution process is conducted in a dispersed-phase system consisting of immiscible aqueous and organic phases vigorously contacted with one another in the presence of enzyme; this can be done in such conventional liquid-liquid contacting equipment as stirred-tank reactors or mixer-settlers. To improve reaction economics, it will be advantageous to immobilize the enzyme on a solid-phase, high-surface-area support in order to facilitate its recovery and reuse, and a process wherein the enzyme is immobilized on particulate supports (e.g., microporous particles, gel-type beads, and ion-exchange resins) is within the scope of the present invention. In such cases, the immobilized enzyme particles may either be dispersed along with the aqueous and organic phases, or they may be packed in a column through which the aqueous and organic phases are made to flow. By the same token, the present invention is not limited to the use of isolated enzymes as biocatalysts, and it will be apparent to those skilled in the art that immobilized whole cells and other micro-organism preparations are also within its scope.

An additional and preferred embodiment of the present invention pertains to conducting the enzymatic resolution process within a multiphase/extractive enzyme membrane reactor. Such multiphase and extractive membrane reactors are described by Matson in U.S. Pat. No. 4,800,162, which is incorporated herein by reference. Multiphase enzyme membrane reactors are particularly advantageous in managing reaction-engineering problems associated with an enzyme's substrate, such as its poor water solubility and/or limited hydrolytic stability. Low solubility and stability in water are both characteristics of the glycidic acid esters that are to be resolved by the practice of the present invention. By the same token, extractive enzyme membrane reactors are particularly useful in managing reaction-engineering problems associated with the products of an enzymatic reaction, such as enzyme inhibition (including inactivation) by inhibitory products or limited conversion in reaction processes that are thermodynamically unfavorable or reversible. Again, as demonstrated subsequently in the experimental examples described Section 5.2 and 5.4, product inhibition is a characteristic exhibited by the enzymatic resolution of the glycidic esters of interest here. Thus, multiphase/extractive membrane reactors have considerable utility in improving the efficiency of the enzymatic reaction.

Generally speaking, the enzyme-activated membrane in the membrane reactor process of this invention will typically consist of a porous and hydrophilic (i.e., water-wet) membrane which is suitably activated by incorporation of an appropriate enzyme within it or on one or more of its surfaces by various means. One surface of this enzymatically active membrane is placed in contact with a first process stream, the feed stream, which typically contains a sparingly water-soluble (i.e., water-immiscible) substrate for the enzyme. Typically, this water-immiscible (organic-based) feed stream contains the reactant dissolved in a water-immiscible organic solvent that serves as a carrier fluid.

Concurrently, the second surface of the enzymatically active membrane is contacted with an aqueous process stream which serves one or more of the following purposes: to supply or remove any water of reaction; to provide means for control of reaction pH (and in some cases access to enzyme contained in the membrane); and to provide means for removal of water-soluble and inhibitory reaction products. When properly operated, the aqueous/organic phase boundary will reside at the surface of the water-wet enzyme-activated membrane that is in contact with the water-immiscible organic feed stream, and a substantially aqueous environment will be provided for operation of the enzyme in the hydrophilic, water-wet membrane. Two inlet (i.e., feed) and two outlet (i.e., product) streams will thus be supplied to and removed from the membrane reactor module in the process of this invention, and the membrane reactor module will thus necessarily be configured with two inlet and two exit ports. One inlet/outlet pair of these ports will be devoted to the supply and withdrawal of the organic-phase process stream, while the other pair will be dedicated to supply and removal of the aqueous process stream.

With hydrophilic or water-wet enzyme-activated membranes, this organic process stream is preferably placed under a small positive pressure relative to the aqueous process stream in contact with the opposite surface of the membrane. This resulting small organic-to-aqueous pressure difference across the membrane serves to prevent the ultrafiltrative flow of a portion of the aqueous process stream across the membrane. At the same time, by operating the process in this manner the organic phase will be prevented from intruding into the pores of the water-wet enzyme membrane by the capillary forces acting at the surface of the membrane in contact with it.

In the practice of the invention herein, the poorly water-soluble and hydrolytically unstable reactant is fed to the membrane reactor in a water-immiscible organic process stream, where it is contacted with a first surface of the enzymatically active membrane. Molecules of the reactant subsequently diffuse to the organic/aqueous interface located at the first surface of the membrane, where they partition into aqueous regions of the membrane and undergo enzyme-catalyzed conversion to products. Where at least one of the reaction products exhibits significant water-solubility, and especially where it is much more water-soluble than the reactant, this product species diffuses out of the membrane and into the aqueous process stream in contact with the second surface of the enzymatically active membrane, to be subsequently removed from the reactor.

In summary, the enzyme-activated membrane in this continuous multiphase bioreactor process serves in three roles: namely, as a high-surface-area organic/aqueous phase contactor, as an organic/aqueous phase separator, and as an interfacial biocatalyst. By placing a hydrophilic membrane at the interface between immiscible aqueous and organic process streams in a membrane module characterized by a high membrane area packing density, it is possible to provide a large organic/aqueous and fluid/membrane contact area without the necessity of dispersing one immiscible phase within the other as is more conventional practice.

More specifically, feeding the racemic d,l-trans methyl ester of 3-(4-methoxyphenyl)glycidic ester to a multiphase/extractive membrane reactor in the form of a solution of the substrate in a water-immiscible organic solvent as shown in the process of FIG. 7 is advantageous for several reasons. On the one hand, the multiphase membrane reactor promotes efficient contact of the poorly water-soluble substrate ester with the membrane-contained enzyme, minimizing diffusional resistances associated with the bulk aqueous phase typically present in non-membrane dispersed-phase operation of such reactions. Additionally, this efficient contact of substrate with enzyme minimizes the undesirable non-catalytic side reactions of the substrate, e.g., hydrolysis of the oxirane ring of the glycidate ester to form diol compounds. Such undesirable hydrolytic side reactions of the substrate can reduce the yield of the enzymatic resolution process and should be minimized, as is possible with the multiphase/extractive membrane reactor of the present invention. The multiphase/extractive membrane reactor provides a high concentration of enzyme at the organic/aqueous interface, thereby maximizing the ratio of the rate of the desired enzymatic hydrolysis of the (2S,3R)-glycidate ester to the rate of the undesired non-catalyzed hydrolysis of the oxirane ring of the (2R,3S)-glycidate ester and maximizing yield of the desired (2R,3S)-glycidate ester reaction product in the process.

A further benefit of conducting the enzymatic resolution process in a multiphase/extractive membrane reactor of FIG. 7 relates to the ability to selectively and efficiently remove or "extract" an inhibitory reaction product from the reaction zone without unnecessarily diluting and/or losing the enzyme catalyst. By removing one or more of the water-soluble ester hydrolysis products (i.e., either or both of the alcohol or glycidic acid species including any subsequent decomposition products such as the aldehyde formed from the glycidic acid) from the reactor via the aqueous process stream, the local concentration of inhibitory product in contact with the enzyme can be maintained at an arbitrarily low level (determined by the economics of recovering and/or disposing of it from the aqueous phase). In essence, the reaction product, formed in the enzyme-activated membrane, is diluted to low concentration by the aqueous process stream flowing past it; thus, the inhibitory product is removed from the reactor, at the same time that the enzyme is kept within the membrane at high concentration. In this manner the reaction may be "pulled" to higher conversions than would otherwise be obtained.

General membrane reactor operating parameters are taught in U.S. Pat. No. 4,800,162 as cited above, and more specific parameters and reaction conditions pertinent to the enzymatic resolution of methyl 3-(4-methoxyphenyl) glycidate esters are given below in Sections 5.2 and 5.4 detailing particular examples of the operation of the process.

A preferred means of reversible enzyme containment is described by Matson in U.S. Pat. No. 4,795,704 and in U.S. patent application Ser. No. 912,595 filed Oct. 1, 1986 and entitled "Method and Apparatus for Catalyst Containment in Multiphase Membrane Reactor System," which are incorporated herein by reference. However, many other means for enzyme immobilization on or within membranes well known in the art may alternately be employed. FIG. 8 shows how enzyme is contained within the asymmetric, microporous, and hydrophilic hollow fiber of a multiphase/extractive membrane reactor; additional detail is provided in examples that follow.

5.2. Examples of Multiphase Enzymatic Resolutions

Several examples of the practice of the invention and elements thereof follow. These examples are meant to illustrate more fully the nature of the present invention without acting as a limitation upon its scope.

5.2.1. Procedures for Examples 1–6

The enzymatic resolution experiments of Examples 1 through 6 described below were conducted in a biphasic system consisting of a dispersion of organic-phase substrate in a continuous aqueous phase. More particularly, a racemic mixture of the trans glycidic ester enantiomers of interest was dissolved in a suitable, water immiscible organic phase, and then contacted with an aqueous phase containing a given enzyme preparation. The entire reaction mixture was agitated or stirred vigorously to provide a large interfacial surface area between the phases, permitting rapid partition of the substrate ester and the acid hydrolysis product between the phases, and permitting the enhancement of the interfacial activity of the enzyme in use, in the event that the particular enzyme displayed such activity. The pH of the aqueous phase was maintained at a level amenable to the enzyme in use by a buffer system.

After an appropriate time, the agitation or stirring was stopped, the organic phase was removed, and the aqueous phase was extracted with more of the same organic solvent or diethyl ether used to form the organic phase. The organic layers were combined, washed with water, dried, and evaporated. The resulting material was then checked for optical activity by polarimetry.

Several simple alkyl esters of the racemic trans-3-(4-methoxyphenyl)glycidic acid were screened as substrates for a variety of enzymes. In particular, the methyl, ethyl, isopropyl, n-butyl, and isobutyl esters of racemic trans-3-(4-methoxyphenyl)glycidic acid were synthesized via the Darzen's glycidic ester condensation (Annalen der Chemie, 583 (1953) 110; *Organic Reactions,* Vol. 5, p. 413, John Wiley & Sons, NY, p. 413, 1968). Each ester was then assayed for susceptibility to enantiospecific hydrolysis by commercially available enzyme preparations according to the following general procedure.

Ten mmoles of the racemic glycidic ester (e.g., 2.08 g in the case of the methyl ester) were dissolved in 50 mls of organic solvent, either toluene or tert-butyl methyl ether, and placed in a flask with 50 mls of 200 mM sodium phosphate buffer of pH 7.0, plus 100 mgs of the enzyme to be assayed. The flask was tightly closed, and placed on a wrist action shaker for 18 hours at ambient temperature (22 to 25° C.). Agitation was then stopped, and the contents of the flask poured into a separatory funnel. The organic layer was removed, and the aqueous layer washed with more of the same organic solvent or diethyl ether. The organic layers were combined, back-washed with water, and dried over anhydrous magnesium sulfate. The organic solvent was then removed under reduced pressure, and the amount of remaining material recorded. A sample of this material was then dissolved in ethanol at a concentration of 1 g per 100 mls (i.e., c=1.0), and checked for optical activity on a polarimeter.

The results of this procedure applied to a number of enzyme/ester combinations in two organic solvents are listed in Examples 1 through 6 below. The commercial sources of isolated enzymes and enzyme preparations are listed beside the enzyme name.

5.2.2. EXAMPLE 1

Stereoselective Hydrolysis of trans-3-(4-methoxyphenyl)glycidic Acid Methyl Ester in tert-butyl Methyl Ether Table 1 presents results for the enzymatic hydrolysis of the methyl ester compound dissolved in tert-butyl methyl ether; a total of 20 different enzyme preparations were employed in these experiments. The amount of racemic methyl ester subjected to enzymatic resolution was 2.08 g in these tests. The experimental protocol employed was that described in Section 5.2.1.

5.2.3. EXAMPLE 2

Stereoselective Hydrolysis of trans-3-(4-methoxyphenyl)glycidic Acid Methyl Ester in Toluene Table 2 presents results for the enzymatic hydrolysis of the methyl ester compound dissolved in toluene; a total of 25 different enzymes and enzyme preparations were employed in these experiments. The amount of racemic methyl ester subjected to enzymatic resolution was 2.08 g in these tests. The experimental protocol employed was that described in Section 5.2.1.

5.2.4. EXAMPLE 3

Stereoselective Hydrolysis of trans-3-(4-methoxyphenyl)glycidic Acid Ethyl Ester in tert-butyl Methyl Ether Table 3 presents results for the enzymatic hydrolysis of the ethyl ester compound dissolved in tert-butyl methyl ether; three different enzyme preparations were employed in these experiments. The amount of racemic ethyl ester subjected to enzymatic resolution was 2.22 g in these tests, which were conducted according the procedure described in Section 5.2.1.

5.2.5. EXAMPLE 4

Stereoselective Hydrolysis of trans-3-(4-methoxyphenyl)glycidic Acid n-butyl Ester in tert-butyl Methyl Ether Table 4 presents results for the enzymatic hydrolysis of the n-butyl ester compound dissolved in tert-butyl methyl ether; three different enzyme preparations were employed in these experiments. The amount of racemic n-butyl ester subjected to enzymatic resolution was 2.50 g in these tests, which were conducted according to the procedure described in Section 5.2.1.

5.2.6. EXAMPLE 5

Stereoselective Hydrolysis of trans-3-(4-methoxyphenyl)glycidic Acid Isopropyl Ester in tert-butyl Methyl Ether Table 5 presents results for the enzymatic hydrolysis of the isopropyl ester compound dissolved in tert-butyl methyl ether; four different enzyme preparations were employed in these experiments. The amount of racemic isopropyl ester subjected to enzymatic resolution was 2.36 g in these tests, which were conducted according to the procedures described in Section 5.2.1.

5.2.7. EXAMPLE 6

Stereoselective Hydrolysis of trans-3-(4-methoxyphenyl)glycidic Acid Isobutyl Ester in tert-butyl Methyl Ether Table 6 presents results for the enzymatic hydrolysis of the isobutyl ester compound dissolved in tert-butyl methyl ether; a single enzyme preparation was employed in this experiment. The amount of racemic isobutyl ester subjected to enzymatic resolution was 2.50 g in this test, which was conducted according to the experimental protocol described in Section 5.2.1.

TABLE 1

| Enzyme | (Enzyme Source) | Recovered Material | [α] (degrees) c = 1 in EtOH |
|---|---|---|---|
| Candida Lipase-OF | (Meito Sangyo) | .960 g | −0.360 |
| Lipase AK | (Amano) | .980 g | −0.500 |
| Lipase AP-12 | (Amano) | 1.00 g | −0.200 |
| Lipase D | (Amano) | .900 g | −0.370 |
| Lipase FAP | (Amano) | .900 g | −0.445 |
| Lipase GC-20 | (Amano) | .980 g | −0.031 |
| Lipase P | (Amano) | .980 g | −0.582 |
| Lipase RH | (Tanabe) | 1.24 g | −0.165 |
| Protease HT | (Miles) | .900 g | −0.148 |
| Protease N | (Amano) | 1.00 g | −0.132 |
| Protease 8 | (Sigma) | 1.22 g | −0.255 |
| Protease 16 | (Sigma) | 800 g | −0.708 |
| Protease 24 | (Sigma) | 940 g | −0.600 |
| Protease 27 | (Sigma) | 880 g | −0.698 |
| Alcalase | (Novo) | 1.26 g | −0.365 |
| Maxatase | (Gist-Brocades) | 1.04 g | −0.208 |
| Prozyme 6 | (Amano) | 1.00 g | −0.077 |
| PLE | (Sigma) | .700 g | −0.168 |
| AFP 2000 | (Miles) | 1.04 g | −0.027 |
| Chr. viscosum | (Toyo Jozo) | 1.10 g | −0.131 |

PLE = Pig liver esterase
Substrate: trans 3-(4-methoxyphenyl)glycidic acid methyl ester
Solvent: tert-butyl methyl ether

TABLE 2

| Enzyme | (Enzyme Source) | Recovered Material | [α] (degrees) c = 1 in EtOH |
|---|---|---|---|
| Lipase N | (Amano) | .800 g | −0.386 |
| Lipase Rh. arr. | (Boehringer Mannheim) | .760 g | −0.470 |
| Lipase R-10 | (Amano) | 1.84 g | −0.010 |
| Lipase K-10 | (Amano) | 1.80 g | −0.128 |
| Lipase L | (Amano) | 1.50 g | −0.035 |
| Lipase MAP | (Amano) | 1.37 g | −0.804 |
| PPL | (Sigma) | 1.58 g | −0.017 |
| Wheat germ | (Sigma) | 1.60 g | −0.010 |
| Papain | (Sigma) | 1.84 g | −0.031 |
| Protease 1 | (Sigma) | 1.72 g | 0.0 |
| Protease 10 | (Sigma) | 1.10 g | −0.010 |
| Protease 14 | (Sigma) | 1.91 g | −0.016 |
| Protease 18 | (Sigma) | .940 g | +0.007 |
| Protease 27 | (Sigma) | 1.91 g | −0.241 |
| Protease 2A | (Amano) | 1.84 g | −0.067 |
| Protease HT | (Miles) | 1.47 g | −0.140 |
| Protease FPC | (Miles) | 1.59 g | −0.011 |
| Acylase 1 | (Sigma) | 1.66 g | 0.0 |
| Palatase A | (Novo) | 1.53 g | −0.014 |
| Palatase M | (Novo) | 1.42 g | −0.791 |
| Sumizyme | (Miles) | 1.52 g | −0.033 |
| Thermoase | (Miles) | 1.60 g | −0.006 |
| *Mucor miehei* | (Biocatalysts) | 1.46 g | −0.762 |
| *Mucor javanicus* | (Biocatalysts) | 1.28 g | −0.972 |
| *H. languinosa* | (Biocatalysts) | 1.41 g | −0.357 |
| LPL 200S | (Amano) | 1.12 g | −0.137 |
| Candida Lipase-OF | (Meito Sangyo) | 1.20 g | −1.029 |

PPL = Porcine pancreatic lipase
Substrate: trans 3-(4-methoxyphenyl)glycidic acid methyl ester
Solvent: toluene

TABLE 3

| Substrate: | trans 3-(4-methoxyphenyl)glycidic acid ethyl ester | | |
|---|---|---|---|
| Solvent: | tert-butyl methyl ether | | |

| Enzyme | (Enzyme Source) | Recovered Material | [α] (degrees) c = 1 in EtOH |
|---|---|---|---|
| Candida Lipase-OF | (Meito Sangyo) | 1.01 g | −0.416 |
| Alcalase | (Novo) | 1.50 g | −0.375 |
| Protease 8 | (Sigma) | 1.45 g | −0.337 |

TABLE 4

| Substrate: | trans 3-(4-methoxyphenyl)glycidic acid n-butyl ester | | |
|---|---|---|---|
| Solvent: | tert-butyl methyl ether | | |

| Enzyme | (Enzyme Source) | Recovered Material | [α] (degrees) c = 1 in EtOH |
|---|---|---|---|
| Candida Lipase-OF | (Meito Sangyo) | 1.59 g | −0.002 |
| LPL 200S | (Amano) | 1.39 g | −0.004 |
| PLE | (Sigma) | 1.57 g | −0.006 |

LPL = Lipoprotein lipase; PLE = Pig liver esterase

TABLE 5

| Substrate: | trans 3-(4-methoxyphenyl)glycidic acid isopropyl ester | | |
|---|---|---|---|
| Solvent: | tert-butyl methyl ether | | |

| Enzyme | (Enzyme Source) | Recovered Material | [α] (degrees) c = 1 in EtOH |
|---|---|---|---|
| Candida Lipase-OF | (Meito Sangyo) | 1.33 g | −0.393 |
| Protease 16 | (Sigma) | 1.83 g | −0.065 |
| Protease 24 | (Sigma) | .850 g | −0.044 |
| Protease 27 | (Sigma) | .780 g | −0.064 |

TABLE 6

| Substrate: | trans 3-(4-methoxyphenyl)glycidic acid isobutyl ester | | |
|---|---|---|---|
| Solvent: | tert-butyl methyl ether | | |

| Enzyme | (Enzyme Source) | Recovered Material | [α] (degrees) c = 1 in EtOH |
|---|---|---|---|
| Candida Lipase-OF | (Meito Sangyo) | 1.01 g | −0.521 |

Particularly preferred enzymes for the stereoselective hydrolysis of the (2S,3R) enantiomer of methyl 3-(4-methoxy-phenyl)glycidate include the lipase designated "Lipase MAP" available from Amano, the lipase designated "Candida Lipase-OF" available from Meito Sangyo, and the protease designated "Protease 27" available from Sigma Chemical Co. These enzymes are attractive for the reasons that they possess good activity towards the simple methyl ester substrate. Additionally, these two enzymes exhibit particularly good stereoselectivity for hydrolysis of the (2S,3R)-glycidate ester in preference to its (2R,3S) counterpart. Both Lipase MAP and Protease 27 leave predominantly negatively rotating species in the organic phase upon completion of the enzymatic reaction, signifying enrichment of the relatively unreactive and negatively rotating (2R,3S)-glycidate ester in the organic phase. The relatively high stereoselectivity of the Protease 27, Lipase MAP, and Lipase-OF enzymes toward the methyl ester compound is evidenced by the relatively large magnitude of the optical rotations reported in Tables 1 and 2, respectively.

The data summarized in Tables 1 through 6 demonstrate that all of the five simple straight- and branched-chain alkyl esters investigated did, in fact, exhibit at least some degree of susceptibility to enzymatic hydrolysis. However, reaction rates and optical rotations obtained with the several substrate/enzyme combinations studied were found to vary considerably. For example, experiments with the n-butyl ester (see Table 4) yielded products with very small optical rotations, indicative of little or no enzyme action and/or stereoselectivity, whereas experiments with the methyl ester gave optical rotations as high as about −0.8° for several enzymes (Table 2). The methyl ester of 3-(4-methoxyphenyl)glycidate is a particularly preferred substrate ester, because methanol is inexpensive and readily available. Additionally, existing commercial processes for the manufacture of diltiazem utilize the methyl glycidate ester directly as an intermediate, as opposed to using other alkyl and aryl glycidate esters. For this reason, production and use of the resolved methyl glycidate ester intermediate in a diltiazem manufacturing process results in a simpler and more economical process than would be obtained with other resolved glycidate ester precursors.

5.2.8. Effect of Cosolvent on Apparent Enantioselectivity E

EXAMPLE 7

An additional aspect of the present invention pertains to the enhancement of enzyme enantioselectivity by the addition of small amounts of organic co-solvents to the aqueous phase, and by the judicious choice of the organic solvent used as the water-immiscible phase.

It is generally known that water-miscible organic solvents can have a significant although unpredictable effect on the enantioselectivity of enzymes. In the case of one of the commercial enzyme preparations, the presence of methanol as 5% of the aqueous phase dramatically increased the apparent E value. The procedure followed to investigate this effect is described below, and the results tabulated.

In Example 7, 100 mgs of Lipase MAP from Amano were added to each of two flasks, each containing 10 mmoles of racemic trans-3-(4-methoxyphenyl)glycidic acid methyl ester that had been dissolved in 50 mls of toluene, plus an aqueous phase of 0.2 M sodium phosphate buffer of pH 7.0 In one flask, the aqueous phase consisted entirely of buffer (50 mls), while in the other flask the aqueous phase was composed of 47.5 mls of buffer plus 2.5 mls of methanol. Each flask was agitated at ambient temperature for 18 hours, and the organic phase was subsequently separated, dried and evaporated to leave a solid material. This solid material was weighed and the degree of hydrolysis "x" was calculated. The optical rotation was measured in ethanol at a concentration of c=1 (i.e., [α]), and the enantiomeric excess of the remaining glycidic ester was calculated (i.e., ee(S)). These results are summarized in Table 7.

TABLE 7

Effect of Methanol on Apparent Enantioselectivity E

|  | x | [α] | ee(S) | E |
|---|---|---|---|---|
| 0% MeOH | .35 | −0.804° | 41% | 11 |
| 5% MeOH | .20 | −0.811° | 41% | >200 |

5.2.9. Effect of Water-Immiscible Organic Solvent on Apparent Enantioselectivity E

EXAMPLE 8

The choice of the water-immiscible organic solvent for the racemic ester substrate represents yet another reaction variable. Using E values as a basis of comparison, the effect of the water-immiscible solvent on the apparent enantioselectivity of a given enzyme may be quantified. The procedure followed to investigate this effect is outlined below.

In Example 8, 100 mgs of enzyme preparation were dissolved or dispersed in 50 mL of 0.2 M sodium phosphate buffer of pH 7.0 To this were added 50 mls of water-immiscible organic solvent in which 10 mmole of racemic trans-3-(4-methoxyphenyl)glycidic acid methyl ester had been dissolved. The reaction flask was capped, and agitated at ambient temperature for 18 hours. The organic layer was then separated, dried, and evaporated in order to recover the non-hydrolyzed glycidic ester. This remaining material was weighed to determine the degree of overall hydrolysis, and its optical rotation was measured in ethanol to determine its enantiomeric excess. The apparent E values calculated for various enzymes in the presence of three different water-immiscible organic phases are summarized in Table 8.

5.2.10. Effect pf pH on Enzyme Enantioselectivity E

EXAMPLE 9

Another factor important to enzyme behavior is the pH of its aqueous environment. It is well known that the activity of enzymes can be strongly pH-dependent, with enhanced catalytic activity in certain pH ranges and lessened activity outside of that range. Less well recognized and more poorly understood is the fact that enzymes may also exhibit pH optima with respect to enantioselectivity as well as activity, particularly since enzyme selectivity is generally thought to arise from steric effects. To investigate this effect with respect to the resolution of racemic trans-3-(4-methoxyphenyl)glycidic acid methyl ester, the aqueous phase in the reaction system was adjusted to varying pH values. The procedure employed is described below.

10 mmoles of the racemic trans-3-(4-methoxyphenyl)-glycidic acid methyl ester were dissolved in 50 ml of toluene and placed in a flask with 50 ml of 200 mM sodium phosphate buffer of varying pH values, along with 100 mg of Lipase MAP obtained from Amano. The flask was tightly closed and placed on a wrist-action shaker for 18 hours at ambient temperature. Agitation was then stopped, and the reaction mixture was worked up as described above. Results are summarized in Table 9, which indicates an optimum pH with respect to enzyme enantioselectivity of about 8.0.

TABLE 8

Effect of Organic Solvent on Apparent Enantioselectivity E
Organic Solvent:

| Enzyme: | Me$^t$BuO$^a$ | Toluene | Chloroform |
|---|---|---|---|
| Lipase MAP | N/D | 11.4 | 2.5 |
| Lipase P | 2.4 | 2.7 | N/D |
| Protease 16 | 2.2 | 3.2 | N/D |
| Protease 27 | 2.5 | 9.7 | 2.3 |

$^a$Methyl tert-butyl ether
N/D = Not determined

TABLE 9

Effect of pH on Enantioselectivity

| pH of Aqueous Phase | Recovered Material | Rotation [α] (c = 1 in ethanol) |
|---|---|---|
| 6.0 | 1.10 g | −0.593° |
| 6.5 | 1.40 g | −0.685° |
| 7.0 | 1.40 g | −0.870° |
| 7.5 | 1.50 g | −0.893° |
| 8.0 | 1.60 g | −0.926° |
| 8.5 | 1.78 g | −0.780° |

Thus, preferred embodiments of this invention include the use of an aqueous phase containing 5% methanol by volume (and, obviously, other concentrations), the use of toluene as the water-immiscible organic solvent, and conduct of the reaction with an aqueous-phase pH of about 8.

5.2.11. Methyl Ester Hydrolysis Catalyzed by Lipase Map

EXAMPLES 10 AND 11

Additional experimental examples were carried out with the preferred substrate (i.e., the methyl ester) and one of the preferred enzymes (i.e., Amano's Lipase MAP) in order to further explore the effect of various reaction parameters and to better understand their influence on the resolution process efficiency Example 10. A hydrolysis experiment was carried out in the following manner. An enzyme solution was prepared by dissolving 276 mg of Lipase MAP (Amano) in 50 ml of 0.01

M sodium phosphate buffer, pH 7.00. A substrate solution containing 2.23 g (10.74 mmoles) of racemic methyl 3-(4-methoxyphenyl)glycidate (MMPG) and 25 ml of toluene was added to the enzyme solution. The pH was controlled in a "pH stat" at 7.00 by the addition of a sodium hydroxide solution (1 mole/L). The addition of NaOH ceased after a total of 0.97 ml of base had been added, corresponding to a conversion of ester to acid of 9.03% (i.e., 100*0.97/10.74). To test whether loss of enzymatic activity was the reason for the reaction's stopping at this point, an additional 127 mg of enzyme were added. No consumption of base was observed after adding the enzyme. The effect of the presence of reaction product on the degree of conversion was tested by introducing an additional 50 ml of water to the reaction mixture to dilute the concentration of reaction products. Immediately after doing so, base consumption began and stopped after the total volume of NaOH added was 1.31 ml. The calculated conversion corresponding to this total acid generation/base consumption was 12.2 % (i.e., 100*1.31/10.74).

Example 11. An additional hydrolysis experiment was carried out in the following manner. An enzyme solution was prepared by dissolving 537 mg of Lipase MAP (Amano) in 1000 ml of 0.01 M sodium phosphate buffer pH 7.00. A substrate solution containing 2.18 g (10.51 mmoles) of racemic methyl 3-(4-methoxyphenyl)-glycidate (MMPG) and 25 ml of toluene was added to the enzyme solution. The pH was controlled in a "pH stat" at 7.00 by the addition of a sodium hydroxide solution (1 mole/L). The addition of NaOH ceased after a total of 3.38 ml of base had been added, corresponding to an ester conversion of 32.16% (i.e., 100*3.38/10.51). To test whether loss of enzymatic activity was the reason for the reaction's stopping at this point, an additional 490 mg of enzyme were added. No additional base consumption was observed after adding the enzyme. The effect of product species concentration on the degree of conversion was tested by introducing an additional 2.25 g of MMPG (10.81 mmoles) in 25 ml of toluene to the reaction mixture. Immediately after doing so, base consumption began and stopped after the total volume of NaOH added was 5.71 ml. The final conversion at this point was 26.78% (i.e., 100*5.71/(10.51+10.81)).

An effective "pseudo-equilibrium" concept is used herein to describe the reaction process, particularly the inhibitory effect of species concentrations on the "equilibrium" conversion. Because the enzymatic hydrolysis reaction was observed to stop once a certain concentration of inhibitory product had accumulated in the system, the reaction process can be described as if the reaction were a thermodynamically "reversible" one, without wishing to be limited as to the specific mechanism of inhibition of the reaction by reaction products or by-products. That is, the reaction can be considered to proceed to a certain "equilibrium" conversion which is dependent on the concentration of inhibitory product or by-product.

5.2.12. Methyl Ester Hydrolysis Catalyzed by Lipase-OF

EXAMPLE 12

An additional hydrolysis experiment with Lipase-OF enzyme was carried out in the following manner. An enzyme solution was prepared by dissolving 64 mg of Lipase-OF (derived from Candida cylindracea, supplied by Meito Sangyo Co.) in 100 ml of 0.05 M sodium phosphate buffer pH 8.00. A substrate solution containing 2.6 g (12.5 mmoles) of racemic methyl 3-(4-methoxyphenyl)glycidate (MMPG) and 25 ml of toluene was added to the enzyme solution. The pH was controlled in a "pH stat" at 8.00 by the addition of a sodium hydroxide solution (0.1 mole/L). After a total of 46.3 ml of base had been added (corresponding to 40% hydrolysis of the ester), the remaining ester was isolated in the manner described above. The enantiomeric excess of the isolated ester product was 87.3% as determined by HPLC. The amount of ester recovered was 1.34 g corresponding to a 52% yield.

5.2.13. Resolution of Racemic Methyl 3-(4-methoxyphenyl)-glycidate in a Membrane Reactor at pH 7

EXAMPLE 13

A multiphase/extractive membrane reactor for this equilibrium-limited enzymatic resolution process could be operated at pH 7.0 in the following manner. The enzyme could be immobilized in the membrane by any one of the conventional methods reported in the literature pertaining to the type of membrane being used. In a preferred embodiment, the enzyme would be immobilized by its reversible containment inside an asymmetric, hydrophilic, microporous hollow-fiber membrane as described by Matson in U.S. Pat. No. 4,795,704 and in copending U.S. patent application Ser. No. 912,595. More particularly, the multiphase/extractive membrane reactor used in this resolution process could consist of a 0.75 $m^2$ custom-made solvent-resistant membrane module fabricated with polyacrylonitrile hollow fibers of the type used in hemofiltration applications and available, for example, from Asahi Co. The enzyme, Lipase MAP, purchased from Amano International Enzymes, has been shown to have an activity of 6 moles of MMPG hydrolyzed per hour per mg of enzyme preparation. This enzyme has also been shown to stereoselectively hydrolyze simple alkyl esters of 3-(4-methoxyphenyl) glycidic acid.

To activate the membrane module with enzyme, 5.0 grams of the enzyme could be dissolved in 1 liter of distilled water. The enzyme solution would then be recirculated in an ultrafiltration mode from the shell into lumen and back to the reservoir for 30 minutes. The ultrafiltrate would be collected until the reservoir is empty, and 250 ml of toluene would subsequently be pumped into the shell and recirculated at 400–450 ml/min with a 5–7 psig shell pressure to remove any remaining enzyme solution from the shell-side space in the reactor module.

After loading the enzyme into the reactor, 100 L of 10 mM phosphate buffer pH 7.00 previously saturated with toluene would be recirculated on the lumen side at a flow rate of 400–500 ml/min. This large volume of aqueous buffer would be required in order to overcome the "reversibility" of the partitioning/reaction process at pH 7, as discussed above. By providing a large aqueous volume, inhibitory products can be diluted to low aqueous-phase concentrations, and the reaction "equilibrium" can thus be displaced to acceptably high conversions. Next, 20.8 g (0.1 mole) of racemic methyl 3-(4-methoxyphenyl)glycidate (MMPG) would be added to the toluene reservoir. The pH of the aqueous reservoir would be kept at 7.00 by the addition of 1.0 M NaOH. The reactor would be run continuously until the degree of ester hydrolysis approached 65%, i.e., until 65 ml of 1 M NaOH had been added. At this point the organic phase would be drained from the membrane reactor, and the remaining MMPG would be isolated from the organic phase in the manner described above.

Feeding the racemic d,l-trans methyl ester of 3-(4-methoxyphenyl)glycidic ester to a multiphase/extractive membrane reactor in the form of a solution of the substrate in a water-immiscible organic solvent is advantageous for several reasons. On the one hand, the multiphase membrane reactor promotes efficient contact of the poorly water-soluble substrate ester with the membrane-contained enzyme, minimizing diffusional resistances associated with the bulk aqueous phase typically present in non-membrane dispersed-phase operation of such reactions. On the other hand, this efficient contact of substrate with enzyme also minimizes the undesirable non-catalytic side reactions of the substrate, e.g., hydrolysis of the oxirane ring of the glycidate ester to form diol compounds. Such undesirable hydrolytic side reactions of the substrate can reduce the yield of the enzymatic resolution process and should be minimized, as is possible with the multiphase/extractive membrane reactor of the present invention. The multiphase/extractive membrane reactor provides a high concentration of enzyme at the organic/aqueous interface, thereby maximizing the ratio of the rate of the desired enzymatic hydrolysis of the (2S,3R)-glycidate ester to the rate of the undesired non-catalyzed hydrolysis of the oxirane ring of the (2R,3S)-glycidate ester and maximizing yield of the desired (2R,3S)-glycidate ester reaction product in the process.

An additional benefit of conducting the enzymatic resolution process in a multiphase/extractive membrane reactor relates to the ability to selectively and efficiently remove inhibitory reaction product from the reaction zone without unnecessarily diluting and/or losing the enzyme catalyst. One the one hand, this may be accomplished by removing a water-soluble inhibitory product via dilution in the aqueous process stream or by chemical reaction therein (e.g., bisulfite adduct formation as discussed in Sections 5.3 and 5.4). Alternatively, inhibitory reaction products that exhibit significant solubility in organic solvents can be removed from the reaction system by extracting them from the organic phase, either in conventional liquid-liquid contacting equipment or in membrane solvent extraction equipment. Certain inhibitory products (e.g., the aldehyde reaction by-product discussed in Sections 5.3 and 5.4) are soluble to a certain degree in both aqueous and organic solutions, and thus are amenable to being managed by either approach.

5.2.14. Resolution of Racemic Methyl 3-(4-methoxy-phenyl)glycidate in a Membrane Reactor at pH 8

EXAMPLES 14–17

Four membrane reactor resolution experiments (corresponding to Examples 14–17) were conducted at pH 8 (as opposed to the pH value of 7 employed in Example 13).

Example 14. A multiphase membrane reactor for this resolution process was operated in the following manner. The membrane reactor consisted of a 0.75 m$^2$ solvent resistant membrane module fabricated with polyacrylonitrile ultrafiltration hollow fibers. The enzyme Lipase MAP, purchased from Amano International Enzymes, has been shown to have an activity of 6 μmoles of MMPG hydrolyzed per hour per mg. This enzyme has also been shown to stereoselectively hydrolyze esters of 3-(4-methoxyphenyl)-glycidic acid.

The membrane reactor was loaded with enzyme in the manner described in Sections 6.6 and 6.7. Specifically, 5.0 grams of the enzyme were dissolved in 1 liter of distilled water. The enzyme solution was then recirculated in an ultrafiltration mode with fluid flowing from the shell into the lumen and back to the reservoir for 30 minutes. The ultrafiltrate was then collected until the reservoir was empty, and 250 ml of toluene were subsequently pumped into the shell and recirculated at 400–450 ml/min with a 5–7 psig shell pressure to remove any remaining enzyme solution from the shell.

After thus loading enzyme into the reactor, 1 L of 0.2 M phosphate buffer at pH 8.00 were recirculated on the lumen side at a rate of 400–500 ml/min. To start the run, 20.8 g (0.1 mole) of methyl 3-(4-methoxyphenyl) glycidate (MMPG) were added to the toluene reservoir. The pH of the aqueous reservoir was kept at 8.00 by addition of 0.9 M NaOH. The reactor ran continuously until the degree of ester hydrolysis reached 57.5% based on the amount of caustic consumed. At this point the organic phase was drained and the remaining MMPG was isolated. The enantiomeric excess of the isolated ester product was 96% as determined by polarimetry. The amount of ester recovered was 4 g, corresponding to a 19% yield.

Example 15. The multiphase membrane reactor described in Example 14 was reused in the following experiment. 375 ml of toluene were pumped into the shell and recirculated at 400–450 ml/min with a 5–7 psig shell pressure to remove any remaining enzyme solution from the shell. An aqueous volume of 1.5 L of 0.2 M phosphate buffer pH 8.00 was recirculated on the lumen side at a rate of 400–500 ml/min. To start the run, 31.2 g (0.15 mole) of methyl 3-(4-methoxyphenyl) glycidate (MMPG) were added to the toluene reservoir. The pH of the aqueous reservoir was kept at 8.00 by the addition of 0.9 M NaOH. The reactor ran continuously until the degree of ester hydrolysis reached 53% based on the amount of caustic consumed. At this point the organic phase was drained and the remaining MMPG was isolated. The enantiomeric excess of the isolated ester product was 99% as determined by polarimetry. The amount of ester recovered was 5.9 g, corresponding to a yield of 19%.

Example 16. The multiphase membrane reactor described in Example 14 was reused in the following experiment. 375 ml of toluene were pumped into the shell and recirculated at 400–450 ml/min with a 5–7 psig shell pressure to remove any remaining enzyme solution from the shell. An aqueous volume of 1.5 L of 0.2 M phosphate buffer pH 8.00 was recirculated on the lumen side at a rate of 400–500 ml/min. To start the run, 31.2 g (0.15 mole) of methyl 3-(4-methoxyphenyl) glycidate (MMPG) were added to the toluene reservoir. The pH of the aqueous reservoir was kept at 8.00 by the addition of 0.9 M NaOH. The reactor ran continuously until the degree of ester hydrolysis reached 52.4% based on the amount of caustic consumed. At this point the organic phase was drained and the remaining MMPG was isolated. The enantiomeric excess of the isolated ester product was 99% as determined by polarimetry. The amount of ester recovered was 9.0 g, corresponding to a yield of 28.8%.

Example 17. The multiphase membrane reactor described in Example 14 was reused in the following experiment. 375 ml of toluene were pumped into the shell and recirculated at 400–450 ml/min with a 5–7 psig shell pressure to remove any remaining enzyme solution from the shell. An aqueous volume of 1.5 L of 0.2 M phosphate buffer pH 8.00 was recirculated on the lumen side at a rate of 400–500 ml/min. To start the run, 31.2 g (0.15 mole) of methyl 3-(4-methoxyphenyl) glycidate (MMPG) were added to the toluene reservoir. The pH of the aqueous reservoir was kept at 8.00 by the addition of 0.9 M NaOH. The reactor ran continuously until the degree of ester hydrolysis reached 41.2% based on the amount of caustic consumed. At this point the organic phase was drained and the remaining MMPG was isolated. The enantiomeric excess of the isolated ester product was 92% as determined by polarimetry. The amount of ester recovered was 7.7 g, corresponding to a yield of 24.8%.

5.3. Management of the Aldehyde Byproduct by Adduct Formation with Bisulfite The enzyme-catalyzed hydrolysis of the ester function of the substrate compound A of FIG. 9—trans-3-(4-methoxyphenyl glycidic acid methyl ester—can be observed by titration of the enzymatic reaction mixture with caustic and by following depletion of the substrate by HPLC methods. However, the corresponding glycidic acid, compound B of FIG. 9, cannot be isolated in significant quantities during work-up of the reaction mixture. In the case of enzymatic reactions allowed to run to relatively high conversion of the reactive substrate enantiomer, removal of the organic solvent from the organic phase reaction product mixture left products in addition to the desired products, the (2R,3S) enantiomer of compound A. The presence of such additional products both reduced the purity of the desired product and made more difficult the recovery of the desired product.

Glycidic acids such as compound B, shown in FIG. 9, are generally known to undergo facile decarboxylation and subsequent rearrangement to the corresponding aldehyde. A two-step mechanism for this reaction has been proposed (Singh and Kagan, *J. Org. Chem.*, 1970, 53, 2203). The resulting compound C, 4-methoxyphenylacetaldehyde, may also be expected to undergo some degree of aerial oxidation by atmospheric oxygen, to give the corresponding carboxylic acid compound D, 4-methoxyphenylacetic acid.

Spectroscopic analysis of the material recovered from the organic phase remaining after the enzyme-catalyzed hydrolysis of compound A, and after removal of the remaining desired (2R,3S) enantiomer of compound A, indicated the presence of both 4-methoxyphenylacetaldehyde, and 4-methoxyphenylacetic acid—that is, compounds C and D, respectively.

Compounds C and D can only be formed from compound A through hydrolysis, whether enzyme- or base-catalyzed, of the methyl ester function of compound A. Furthermore, the aldehyde compound C may react further. Such further reaction may include not only the specific example of oxidation to the corresponding carboxylic acid compound D, experimentally observed by spectroscopic methods, but also adduct formation reactions, hydration to the gem-diol, oligomerization (such as the formation of the trimeric compound analogous to that formed by formaldehyde), and aldol condensation, under either acidic or basic conditions, leading to a large number of possible oligomeric or polymeric products. Additionally, aldehydes can participate in Schiff-base formation, a well-known chemical reaction (J. March, *Advanced Organic Chemistry*, McGraw-Hill Co., 2nd Ed. 1977; Hendrickson, Cramm, and Hammond, *Organic Chemistry*, McGraw-Hill Co., 3rd Ed. 1970). Generally, most Schiff-bases are stable near neutral pH, and hydrolyze under either acid or base conditions. However, the mechanism of formation involves nucleophilic attack of a non-protonated amine nitrogen on the carbonyl compound in question, such as an aldehyde, and thus Schiff-base formation proceeds more rapidly at pH conditions above pH 7.

As it relates to enzyme reactions, the presence in the reaction system of the aldehyde compound C is cause for concern, inasmuch as Schiff-base formation between aldehydes and the $\epsilon$-amino groups of lysine residues is well known [T. E. Creighton, *Proteins: Structures and Molecular Properties*, Freeman and Co., 1983]. The resulting modification of an enzyme may give rise to both reversible and irreversible deleterious effects on an enzyme's ability to catalyze a given reaction.

As used herein, the terms "inhibition" and "inhibitory" are meant to describe any process or phenomenon whereby a chemical compound—more particularly a reaction product or byproduct—causes a decrease in the ability of an enzyme to catalyze a given reaction. For example, such inhibition may include that described by the well-known Michaelis-Menten model of enzyme kinetics. This inhibitory effect of a compound on the enzyme may be evident either while the inhibitory compound is in contact with the enzyme during the reaction, or the inhibitory effect may persist after said inhibitory compound has been in contact with the enzyme and subsequently removed. For example, such inhibitory properties may include those associated with compounds which chemically modify the functional groups of amino acid residues of the enzyme protein. Thus, alleviation of both reversible and irreversible forms of inhibition are contemplated in the practice of the present invention.

Inhibitory effects leading to a shortened enzyme life under a given set of reaction conditions will require that the enzyme be replaced more frequently than an enzyme which has a longer lifetime. Taking the average rate of reaction as a measure of enzymatic activity, Table 10 clearly shows that the commercial enzyme preparation Lipase OF operating under the reaction conditions described in Examples 18 and 19 maintains its activity over longer periods of time when the aldehyde byproduct is removed by the addition of bisulfite.

The presence of the aldehyde by-product has important consequences in the operation of a membrane bioreactor used for the resolution of esters of 3-(4-methoxyphenyl) glycidate. In two resolutions done under the reactor conditions described in Example 18, the aqueous phase turned into a white suspension after 15% of the charged ester was titrated. Filtering aliquats of this white suspension through an ultrafiltration membrane removed the white precipitate. However, upon standing for 1 hour, a white suspension appeared in the clear filtrate once again. The demonstrated retention of the precipitate by ultrafiltration suggests that a membrane could be fouled both internally and externally by this material. In experiments done under conditions identical to those in Example 18, but without activating the membrane with enzyme, no white suspension was observed even after 24 hours. Without wishing to be bound to any particular mechanism or explanation, the formation of the white precipitate is consistent with the aldehyde by-product, having a limited but finite water-solubility, being transformed into a water-insoluble product.

In other experiments conducted under the conditions described in Example 18, a solid precipitate was observed present in the aqueous phase. This solid is capable of fouling the inside surface of the membrane and thus reducing its enzymatic activity. In one experiment conducted under the conditions described in Example 18, reversing the aqueous phase flow direction through the fiber lumen resulted in a sudden appearance of yellow particles in the aqueous stream and also a sudden increase in enzymatic activity (as evidenced by an increase in acid titration rate).

The presence of the aldehyde by-product (compound C) also has important implications with regards to the isolation procedure of the final product. As the aldehyde is appreciably organic soluble, it may interfere in the recovery process of the desired product, the (2R,3S) enantiomer of compound A. Increasing amounts of the aldehyde (compound C) in the final organic phase of the reaction mixture make a complete separation of the final product from the aldehyde impurity more difficult and less economical.

For the specific case of enzymatic resolution of glycidate esters, the existence of an aldehyde by-product, compound C, in the reaction mixture suggests a purification method for improving the quality of the final, desired product of the enzyme reaction. This method involves the selective removal of the aldehyde compound C from the organic phase of the enzyme reaction mixture through the selective formation of a bisulfite adduct. This adduct is formed by contacting the organic phase of the enzyme reaction mixture with an aqueous solution of a bisulfite salt, and subsequently extracting the bisulfite adduct into the aqueous phase.

The addition of bisulfite to aldehydes compounds is well known, and mentioned in most organic chemistry textbooks. In general, the carbonyl group of most aldehydes, and some ketones, undergoes nucleophilic attack by the bisulfite anion, leading to the α-hydroxy sulfonate compound E as shown in FIG. 9. Such a compound is generally known as a bisulfite adduct. The stability and ease of formation of such adducts is believed to be determined by the chemical properties of the carbonyl group undergoing the nucleophilic attack. Steric effects are believed to determine the ease of formation of such adducts, and they are generally formed under slightly acidic conditions (Fieser and Fieser, *Reagents for Organic Synthesis*, Vol. 1, John Wiley, 1967), near pH 5, where the nucleophilic $HSO_3$-anion is the predominant species in aqueous solution, and the carbonyl group may be slightly protonated, enhancing nucleophilic attack. However, the optimal conditions for both the formation and stability of such adducts are generally considered empirical, and bisulfite adducts are also known to be formed under mildly basic conditions.

Accordingly, a bisulfite solution can be used to wash the organic phase of a dispersed-phase enzymatic reaction after the desired degree of ester hydrolysis is reached, and prior to the removal of the organic solvent comprising the bulk organic phase for the recovery of compound A enriched in the desired (2R,3S) enantiomer. This approach to removing contaminating aldehyde from the desired glycidate ester product is described in Example 20.

However, it was found that a 10% bisulfite solution would also degrade compound A, in the absence of any other hydrolysis reaction products, possibly through attack on the epoxide function by the bisulfite anion, thus leading to a loss of both enantiomers of compound A during reaction work-up. This problem is illustrated in Example 21. This example suggests the existence of an upper limit of bisulfite concentration in a reaction process which cannot exceeded without compromising final product yield.

Example 22 illustrates the decrease in rate of enzyme catalyzed hydrolysis of compound A in the presence of compound C, and the comparative lack of such an inhibitory effect in the presence of compound D. It should be noted that the apparent enhancement by compound D of the rate of hydrolysis by Lipase OF shown in this example is reproducible, and indicates that compound D does not have an inhibitory effect. In addition, the bisulfite adduct, compound E, is not inhibitory, indicating that the stability of the bisulfite adduct under these conditions is sufficient to prevent compound C from exerting its inhibitory effects.

In light of the above information and examples, the possibility exists of removing the inhibitory compound C in situ by formation of its bisulfite adduct during enzymatic hydrolysis of the ester function of compound A. Several factors must be considered in choosing reaction conditions so that the stability of the substrate (compound A), the desired enzymatic activity and enzyme stability, and the ease of formation and stability of the bisulfite adduct of compound C are all maximized. Such work is necessarily empirical, although some information does exist in the open literature. That is, ester functions are generally known to be most stable at close to neutral pH, while epoxides are generally most stable in aqueous solutions between pH 8 and 9.5 (Y. Pocker, B. P. Ronald, and K. W. Anderson, *J. Amer. Chem. Soc.*, 1988, 110, 6492). Aldehyde-bisulfite adducts are generally known to be stable between pH 5 to 9.

The experimental results shown in Table 11 indicate that the bisulfite adduct, compound E, is sufficiently stable at pH 8 to alleviate the inhibitory effects of compoundc. As regards choosing an appropriate bisulfite concentration, the results from Example 21 suggest that 10% w/v is an upper bound if product yield is not to be compromised. At the other extreme, the absence of bisulfite allows the inhibitory effect of compound C to be expressed. Since the stoichiometry of the aldehyde-bisulfite chemistry is one-to-one, a preferred amount of bisulfite anion to be used in the aqueous phase would be an amount equimolar with the amount of aldehyde by-product expected to be generated during the reaction, provided that the volume of aqueous phase is such that the bisulfite concentration does not exceed the upper bound mentioned above.

It should be noted that the bisulfite anion, which exists in aqueous solutions near neutral pH, may be formed by the removal of one proton from sulfurous acid, that is $H_2SO_3$—which itself may be formed through the dissolution and hydration of sulfur dioxide in water. Sulfurous acid may form salts with alkali metals as the corresponding cationic species (e.g., $Na^+$). The anionic species of such salts include bisulfite ($HSO_3-$), sulfite ($SO_3^{-2}$), and metabisulfite ($S_2O_5^-$ 2) It should be noted that in an aqueous solution, a mixture of all such forms of sulfurous acid and its salts will exist is an equilibrium mixture, the composition of which will depend on the pH of the solution. An equilibrium between solvated bisulfite anion and sulfite dianion will exist in an aqueous solution over the pH range of 5 to 9, the $pK_a$ of the bisulfite anion being approximately 7. In addition to this equilibrium, one molecule of metabisulfite salt may become hydrated and disproportionate in water to yield two molecules of bisulfite salt. All salts may dissolve to varying degrees to yield the solvated alkali metal cationic species together with solvated bisulfite, sulfite, and metabisulfite anionic species, all of which may subsequently participate in the formation of an equilibrium mixture. In view of the complex equilibria in which the bisulfite anion may participate, the terms "bisulfite concentration" and "bisulfite anion concentration" as used herein are meant to refer to the total concentration of an equilibrium mixture of sulfite, bisulfite, and metabisulfite species—that is, all salts and solvated species, including all the various protonated and ionized species which may be derived from sulfurous acid in aqueous solution—as opposed to referring only to the concentration of the individual anionic bisulfite species $HSO_3$— by itself. As all of the above-mentioned species may ultimately be derived from sulfur dioxide, the concentration of bisulfite in an aqueous solution may also be described in terms of the solution's "sulfur dioxide content."

The ratio of organic to aqueous phase volumes is not critical and may be set at any convenient value, consistent with providing in a preferred embodiment at least one equivalent of bisulfite (in the aqueous phase) per mole of compound A (the latter being supplied in the organic phase) to be hydrolyzed in the reaction, and consistent with the concentration of bisulfite in the aqueous phase not exceeding that which causes substrate degradation—e.g., about 10% w/v.

In view of the above considerations, the bisulfite concentration was set at 0.5% w/w (0.048 M sodium sulfite) of the aqueous phase for Examples 23 to 26, giving a slight molar excess of bisulfite at 50% hydrolysis of racemic compound A, assuming that all of the hydrolyzed compound A is transformed to compound C and that the 1 liter of aqueous phase is used for every 0.094 moles of racemic ester in the organic phase. The resulting conditions chosen for dispersed-phase enzyme reactions consisted of an aqueous phase consisting of 50 mM pH 8.0 sodium phosphate buffer containing 0.5% w/w sodium bisulfite at ambient temperature, and an organic-to-aqueous phase ratio of approximately 1:10; these conditions were shown to give improved yields of the desired (2R,3S) enantiomer of compound A and to minimize the inhibitory effects of compound C. The results from these experiments are summarized in Examples 23–26 and in Table 12.

The data presented in Examples 18–19, Examples 23–26, and Tables 10–12 show that the presence of bisulfite in the aqueous phase during the enzymatic resolution of esters of 3-(4-methoxyphenyl)glycidate has a very beneficial effect on the enzymatic activity of Lipase OF, and positive effects on product yield and chemical and enantiomeric purity as well.

The effect of bisulfite anion at a total concentration of 0.093 M on the stability of representative enzymes that might be used in this resolution process was determined, and results are summarized below:

| | | Percent of Activity Remaining | |
|---|---|---|---|
| Enzyme | pH | 24 hr | 48 hr |
| Palatase M[N] | 7.0 | 40.1 | 0.0 |
| Palatase M | 8.0 | 10.4 | 0.0 |
| Lipase MAP[A] | 7.0 | 79.4 | 0.0 |
| Lipase MAP | 8.0 | 40.1 | 0.0 |
| Lipase OF[M] | 7.0 | 85.1 | 32.2 |
| Lipase OF | 8.0 | 74.5 | 28.9 |
| Lipase P[A] | 8.0 | 98.1 | 95.2 |

[A]Amano International Enzyme Co.
[M]Meito Sangyo
[N]Novo Industries

The above results suggest that all enzymes are not equivalent in terms of their stability in the presence of bisulfite anion. Additional evidence is shown in Table 13, which summarizes results from Example 27. When compared against the results shown in Table 10 for Lipase OF in the presence of bisulfite anion, it becomes clear that sulfite did not enhance the catalytic activity of Palatase M.

In order to reduce the deleterious effect that bisulfite may have on certain enzymes, it is possible to add the bisulfite to the aqueous phase continuously to the aqueous phase as a function of the amount of ester that has been reacted as opposed to charging all of the bisulfite-containing species to the aqueous phase at the beginning of the reaction. That is, it is within the scope of the present invention to gradually add the amount of bisulfite needed to react with the amount of aldehyde being generated by the enzymatic reaction. This form of bisulfite addition has the advantage of keeping to a minimum the amount and concentration of free bisulfite that is available to interact with the enzyme.

5.4. Examples Pertinent of Bisulfite Utilization

Several examples of the practice of the invention and elements thereof follow. These examples are meant to illustrate more fully the nature of the present invention without acting as a limitation upon its scope.

5.4.1. Resolution of trans-3-(4-methoxyphenyl) glycidic Acid Methyl Ester in a Multiphase Enzyme Membrane Reactor 5.4.2. EXAMPLE 18

Resolution of trans-3-(4-methoxyphenyl)glycidic Acid Methyl Ester in a Multiphase Enzyme Membrane Reactor in the Absence of Bisulfite The enzymatic resolution of Example 18A was conducted in the type multiphase/extractive enzyme membrane reactor described above. The membrane was activated with 10 grams of Lipase OF. The membrane activation procedure is described by Matson in U.S. Pat. No. 4,795,704 and in U.S. patent application Ser. No. 912,595, filed Oct. 1, 1986 and entitled "Method and Apparatus for Catalyst Containment in Multiphase Membrane Reactor System." The organic phase was prepared by dissolving 78 grams (0.375 moles) of a racemic mixture of the trans-3-(4-methoxyphenyl)glycidic acid methyl ester (compound A) in 375 ml of toluene. This organic solution was then recirculated on the shell side of a hollow fiber device. Four liters of an aqueous 50 mM sodium phosphate buffer of pH 8.0 were recirculated on the lumen side of the membrane device. The pH was maintained at 8.0 by adding sodium hydroxide with a device for monitoring and maintaining a given pH, commonly known as a "pH stat".

After 11 hours the organic fluid was drained from the membrane device. To reduce losses, the membrane device was rinsed with 500 ml of fresh toluene and the two toluene fractions were then combined. The toluene was subsequently evaporated under vacuum at 65° C. To the remaining solids methanol was added so that the solids concentration would be 20% (w/w). This solution was then chilled at −20° C. for three hours. The precipitated crystals were filtered, dried, and analyzed for optical purity. These final crystals are hereby referred to as the reactor product.

The mother liquors from the crystallization were evaporated under vacuum to remove the methanol. The remaining liquid was then analyzed for ester concentration. The balance of this liquid includes the inhibitory aldehyde by-product compound C.

A second enzymatic resolution (Example 18B), conducted in the same membrane reactor still containing the same enzyme used in Example 18A, was started 13 hours after completion of the first resolution. This second reaction was stopped after 22 hours and the organic phase was processed in the same manner as in the first resolution. The results from these two resolutions are summarized in Table 10.

5.4.3. EXAMPLE 19

Resolution of trans-3-(4-methoxyphenyl)glycidic Acid Methyl Ester in a Multiphase Enzyme Membrane Reactor Using Sodium Bisulfite The enzymatic resolution of Example 19A was conducted in the same type of multiphase/extractive enzyme membrane reactor described above. The membrane was activated with 10 grams of Lipase OF. The membrane activation procedure is described by Matson in U.S. Pat. No. 4,795,704 and in U.S. patent application Ser. No. 912,595, filed Oct. 1, 1986 and entitled "Method and Apparatus for Catalyst Containment in Multiphase Membrane Reactor System." The organic phase was prepared by dissolving 78 grams (0.375 moles) of a racemic mixture of the trans-3-(4-methoxyphenyl)glycidic acid methyl ester (compound A) in 375 ml of toluene. This organic solution was then recirculated on the shell side of a hollow fiber device. Four liters of a pH 8.0 buffer solution containing 0.2 moles of sodium phosphate and 0.375 moles of sodium bisulfite were recirculated on the lumen side of the membrane device.

The reaction was stopped after 7.5 hours and the organic fluid was drained from the membrane device. To reduce losses, the membrane device was rinsed with 500 ml of fresh toluene and the two toluene fractions were then combined. The toluene was subsequently evaporated under vacuum at 65° C. To the remaining solids methanol was added so that the solids concentration would be 20% (w/w). This solution was then chilled at −20° C. for three hours. The precipitated crystals were filtered, dried, and analyzed for optical purity. These final crystals are hereby referred to as the reactor product.

The mother liquors from the crystallization were evaporated under vacuum to remove the methanol. The remaining liquid was then analyzed for ester concentration. The balance of this liquid includes the inhibitory aldehyde by-product compound C.

A second enzymatic resolution (Example 19B), conducted in the same membrane reactor used in Example 19A and still containing the same enzyme, was started 16 hours after completion of the first resolution. This second reaction was stopped after 7.5 hours and the organic phase was processed in the same manner as in the first resolution.

A third enzymatic resolution (Example 19C), conducted in the same membrane reactor used in Examples 19A and 19B and still containing the same enzyme, was started 16 hours after completion of the second resolution. This third reaction was stopped after 7.5 hours and the organic phase was processed in the same manner as in the first and second resolution. The results from all three resolutions are summarized in Table 10.

TABLE 10

| Example No. | 18A | 18B | 19A | 19B | 19C |
|---|---|---|---|---|---|
| Resolution No. | 1 | 2 | 1 | 2 | 3 |
| Sulfite used? | NO | NO | YES | YES | YES |
| Reaction time (hr) | 11.0 | 22.0 | 7.5 | 7.5 | 7.5 |
| Conversion (%) | 57.1 | 59.8 | 54.5 | 54.7 | 54.0 |
| Average rate of reaction (mmole/hr) | 19.5 | 10.2 | 27.3 | 27.4 | 27.0 |
| Product yield (%) | 36.4 | 35.0 | 39.2 | 38.5 | 39.1 |
| Weight of inhibitory aldehydic product recovered (g) | 18.6 | 20.9 | 1.6 | 2.9 | 1.5 |
| Enantioselectivity E | 10.9 | 14.8 | 26.6 | 19.4 | 23.9 |

Definitions

Conversion is defined as the amount of glycidate ester that was reacted, divided by the initial amount of racemic ester charged to the reactor (78 g, 0.375 moles).

Average rate of reaction is the amount of glycidate ester that was reacted divided by the total reaction time.

Product yield is the amount of resolved material isolated from the reactor (following the procedure described in Example 18) divided by the amount of racemic ester charged to the reactor (78 g, 0.375 moles).

Weight of inhibitory aldehydic product is the amount of non-ester material isolated from the reactor.

5.4.4. EXAMPLE 20

Enrichment of Reaction Product from Enzymatic Resolution of trans-3-(4-methoxyphenyl)glycidic Acid Methyl Ester Using Sodium Bisulfite 50 ml of toluene containing 10 mmoles of racemic compound A were shaken with 50 mls of 0.2 M sodium phosphate buffer of pH 8.0, containing 100 mgs of the commercial enzyme preparation from Amano known as Lipase MAP, for 18 hours at ambient temperature. The reaction mixture was then diluted with water to 400 mls volume, and extracted twice with 400 mls diethyl ether. The combined organic phases were then back extracted twice with 400 mls water, dried over magnesium sulphate, and evaporated to leave 1.5 g (7.2 mmoles) of crude product material. The optical rotation of this material in ethanol at c=1.0 was −68.0 degrees, indicating an enantiomeric excess of 34.7%. (The value of −196.2 degrees was used as the standard for 100% enantiomeric excess of the (2R,3S) enantiomer as measured in ethanol). The crude product was then re-dissolved in 300 mls diethyl ether, and the organic solution washed twice with 100 mls of a 10% sodium bisulfite solution. The organic phase was then backwashed with water, dried over magnesium sulphate, and evaporated to leave 1.4 g (6.7 mmoles) of a more pure product material. The optical rotation of this material in ethanol at c=1.0 was −117.5 degrees, indicating an enantiomeric excess of 59.9% of the desired (2R,3S) enantiomer of compound A.

5.4.5. EXAMPLE 21

Recovery of trans-3-(4-methoxyphenyl)glycidic Acid Methyl Ester from Toluene Using Concentrated Sodium Bisulfite 2.0 g of pure, racemic compound A were dissolved in 200 mls of diethyl ether. This organic solution was then extracted once with 250 mls of a 10% bisulfite solution, washed with 250 mls water, dried over magnesium sulphate, and evaporated to leave 1.8 g of racemic compound A, indicating a 10% loss of material. Recovery of material in the absence of the bisulfite wash was nearly quantitative.

5.4.6. EXAMPLE 22

Degree of Inhibition on Representative Enzymes by Reaction Products

A reaction mixture composed of 12 mls of 50 mM sodium phosphate buffer at pH 8.0 and 8 mls of a 400 mM toluene solution of pure, racemic compound A, was rapidly stirred and the reaction rate monitored by a device known as a "pH stat". A given amount of a given commercial enzyme preparation was then added to the reaction mixture, and the initial rate of hydrolysis calculated. The reaction was repeated in the presence of 1 mmole (50 mM) of compound C, in the presence of 1 mmole (50 mM) of compound D, and in the presence of 1 mmole (50 mM) of compound E. The results are tabulated in Table 11.

TABLE 11

| Enzyme | Relative Initial Rates* | | | |
|---|---|---|---|---|
| Compound(s): | A | A + C | A + D | A + E |
| Lipase OF | 1.0 | 0.63 | 1.18 | >1.50 |
| Lipase MAP | 1.0 | 0.73 | 0.99 | 1.03 |
| Lipase P | 1.0 | 1.00 | 1.07 | 1.06 |
| Palatase M | 1.0 | 0.38 | >1.0 | 0.69 |

*Note: relative initial rates are not normalized between enzymes

5.4.7. EXAMPLE 23

Resolution of trans-3-(4-Methoxyphenyl)glycidic Acid Methyl Ester Using Sodium Bisulfite 400 mls of a solution of 50 mM sodium phosphate buffer at pH 8.0 and containing 0.5% weight by volume sodium bisulfite, was stirred together with 42.5 mls of toluene containing 7.8 g (37.5 mmoles, approx. 0.88 M) in a 600 ml beaker, and monitored by a pH stat equipped to titrate the reaction with sodium hydroxide in order to hold the pH at 8.0. To this were added 100 mgs of the commercial preparation of Lipase OF, and the reaction allowed to proceed for 90 minutes. The reaction mixture was then poured into a separatory funnel, extracted twice with 400 mls of diethyl ether, and the combined organic phases dried over magnesium sulphate. Evaporation of the ether left compound A enriched in the desired (2R,3S) enantiomer. This crude product was then re-crystallized once in the conventional manner from a minimal volume of hot methanol, and the re-crystallized products recovered by filtration. The enantiomeric excess of the various crude and re-crystallized products were measured in ethanol at c=1.0, using the standard value of –196.2 degrees as 100% enantiomeric excess of the (2R,3S) enantiomer. The percentage yield listed is the yield of product expressed as a percent of the original amount of substrate. The percentage yield of the (2R,3S) enantiomer is expressed as the percentage of the amount of this enantiomer originally present in the racemic substrate, and is the product of percent yield times percent e.e. The results are summarized in Table 12.

5.4.8. EXAMPLE 24

Resolution of trans-3-(4-Methoxyphenyl)glycidic Acid Methyl Ester in the Absence of Sodium Bisulfite 400 mls of a solution of 50 mM sodium phosphate buffer at pH 8.0 was stirred together with 42.5 mls of toluene containing 7.8 g (37.5 mmoles, approx. 0.88 M) in a 600 ml beaker, and monitored by a pH stat equipped to titrate the reaction with sodium hydroxide in order to hold the pH at 8.0. To this were added 100 mgs of the commercial preparation of Lipase OF, and the reaction allowed to proceed for 90 minutes. The reaction mixture was then poured into a separatory funnel, extracted twice with 400 mls of diethyl ether, and the combined organic phases dried over magnesium sulphate. Evaporation of the ether left compound A enriched in the desired (2R,3S) enantiomer. This crude product was then re-crystallized once in the conventional manner from a minimal volume of hot methanol, and the re-crystallized products recovered by filtration. The enantiomeric excess of the various crude and re-crystallized products were measured in ethanol at c=1.0, using the standard value of –196.2 degrees as 100% enantiomeric excess of the (2R,3S) enantiomer. The percentage yield listed is the yield of product expressed as a percent of the original amount of substrate. The percentage yield of the (2R,3S) enantiomer is expressed as the percentage of the amount of this enantiomer originally present in the racemic substrate, and is the product of percent yield times percent e.e. The results are summarized in Table 12.

5.4.9. EXAMPLE 25

Resolution of trans-3-(4-Methoxyphenyl)glycidic Acid Methyl Ester Using Sodium Bisulfite and Extended Reaction Time 400 mls of a solution of 50mM sodium phosphate buffer at pH 8.0 and containing 0.5% weight by volume sodium bisulfite, was stirred together with 42.5 mls of toluene containing 7.8 g (37.5 mmoles, approx. 0.88 M) in a 600 ml beaker, and monitored by a pH stat equipped to titrate the reaction with sodium hydroxide in order to hold the pH at 8.0. To this were added 100 mgs of the commercial preparation of Lipase OF, and the reaction allowed to proceed for 4 hours. The reaction mixture was then poured into a separatory funnel, extracted twice with 400 mls of diethyl ether, and the combined organic phases dried over magnesium sulphate. Evaporation of the ether left compound A enriched in the desired (2R,3S) enantiomer. This crude product was then re-crystallized once in the conventional manner from a minimal volume of hot methanol, and the re-crystallized products recovered by filtration. The enantiomeric excess of the various crude and re-crystallized products were measured in ethanol at c=1.0, using the standard value of –196.2 degrees as 100% enantiomeric excess of the (2R,3S) enantiomer. The percentage yield listed is the yield of product expressed as a percent of the original amount of substrate. The percentage yield of the (2R,3S) enantiomer is expressed as the percentage of the amount of this enantiomer originally present in the racemic substrate, and is the product of percent yield times percent e.e. The results are summarized in Table 12.

5.4.10. EXAMPLE 26

Resolution of trans -3-(4-Methoxyphenyl)glycidic Acid Methyl Ester Using Sodium Bisulfite in a Larger Scale 1200 mls of a solution of 50 mM sodium phosphate buffer at pH 8.0 and containing 0.5% weight by volume sodium bisulfite, was stirred together with 127.5 mls of toluene containing 23.4 g (112.5 mmoles, approx. 0.88 M) in a 2000 ml beaker, and monitored by a pH stat equipped to titrate the reaction with sodium hydroxide in order to hold the pH at 8.0. To this were added 300 mgs of the commercial preparation of Lipase OF, and the reaction was allowed to proceed for 90 minutes. The reaction mixture was then poured into a separatory funnel, extracted twice with 1200 mls of diethyl ether, and the combined organic phases dried over magnesium sulphate. Evaporation of the ether left compound A enriched in the desired (2R,3S) enantiomer. This crude product was then re-crystallized once in the conventional manner from a minimal volume of hot methanol, and the re-crystallized products recovered by filtration. The enantiomeric excess of the various crude and re-crystallized products were measured in ethanol at c=1.0, using the standard value of –196.2 degrees as 100% enantiomeric excess of the (2R,3S enantiomer. The percentage yield listed is the yield of product expressed as a percent of the original amount of substrate. The percentage yield of the (2R,3S)

enantiomer is expressed as the percentage of the amount of this enantiomer originally present in the racemic substrate, and is the product of percent yield times percent e.e. The results are summarized in Table 12.

TABLE 12

| Example | Recovered Compound A | % yield | $[\alpha]_D$ (EtOH) | % e.e. | % (2R,3S) |
|---|---|---|---|---|---|
| 23 | 3.4 g | 43.6% | −193.0 | 98% | 42.7% |
| 24 | 3.4 g | 43.0% | −162.0 | 82% | 35.2% |
| 25 | 3.1 g | 39.7% | −182.4 | 93% | 36.9% |
| 26 | 11.0 g | 47.0% | −161.7 | 82% | 38.5% |

5.4.11. EXAMPLE 27

Resolution of trans-3-(4-Methoxyphenyl)glycidic Acid Methyl Ester in a Multiphase Enzyme Membrane Reactor Using Palatase M The enzymatic resolution of Example 27A was conducted in the same type of multiphase/extractive enzyme membrane reactor described above. The membrane was activated with 150 ml of Palatase M solution (Novo). The membrane activation procedure is described by Matson in U.S. Pat. No. 4,795,704 and in U.S. patent application Ser. No. 912,595, filed Oct. 1, 1986 and entitled "Method and Apparatus for Catalyst Containment in Multiphase Membrane Reactor System." The organic phase was prepared by dissolving 78 grams (0.375 moles) of a racemic mixture of the trans-glycidic methyl ester in 375 ml of toluene. This organic solution was then recirculated on the shell side of a hollow fiber device. Four liters of a pH 8.0 buffer solution containing 0.2 moles of sodium phosphate and 0.375 moles of sodium bisulfite were recirculated on the lumen side of the membrane device.

After 7.5 hours the organic fluid was drained from the membrane device. To reduce losses, the membrane device was rinsed with 500 ml of fresh toluene and the two toluene fractions were then combined. The toluene was subsequently evaporated under vacuum at 65° C. To the remaining solids methanol was added so that the solids concentration would be 20% (w/w). This solution was then chilled at −20° C. for three hours. The precipitated crystals were filtered, dried, and analyzed for optical purity. These final crystals are hereby referred to as the reactor product.

The mother liquors from the crystallization were evaporated under vacuum to remove the methanol. The remaining liquid was then analyzed for ester concentration. The balance of this liquid is assumed to be the inhibitory aldehydic product.

A second enzymatic resolution (Example 27B), conducted in the same membrane reactor of Example 27A and still containing the same enzyme, was started 16 hours after completion of the first resolution. This second reaction was stopped after 7.5 hours and the organic phase was processed in the same manner as in the first resolution.

A third enzymatic resolution (Example 27C), conducted in the same membrane reactor of Examples 27A and 27B and still containing the same enzyme, was started 16 hours after completion of the second resolution. This third reaction was stopped after 7.5 hours and the organic phase was processed in the same manner as in the first and second resolution. The results from all three resolutions are summarized in Table 13.

TABLE 13

| Example No. | 27A | 27B | 27C |
|---|---|---|---|
| Sulfite used? | YES | YES | YES |
| Reaction time (hr) | 7.5 | 7.5 | 7.5 |
| Conversion | 51.8 | 47.7 | 41.6 |
| Average rate of reaction (mmole/hr) | 25.9 | 23.8 | 20.8 |
| Product yield (%) | 39.2 | 40.4 | 35.13 |
| Enantioselectivity E | 26.0 | 27.8 | 10.8 |

5.4.12. EXAMPLE 28

Batch Reactions in Toluene Followed by Direct Crystallization of trans-3-(4-Methoxyphenyl) glycidic Acid Ester (GLOP) Therefrom The batch reactions described herein were carried out in a multiphase-extractive enzyme membrane reactor similar to that described above. Reactor configurations and procedures have also been devised in which mother liquors from product crystallizations (See, further, below) are recycled, thus making the enzymatic enantioselective resolution methods of the present invention even more economically attractive. It should be understood, however, that this multiphase enzymatic resolution can also be carried out under dispersed conditions induced by agitation, sonication, or in the presence of dispersing or emulsifying agents so long as these additional components do not interfere in a substantial way with the resolution of the substrate (e.g., racemic GLOP).

The membrane was activated with 10 grams of Lipase OF. As stated earlier, membrane activation procedures as described by Matson in U.S. Pat. No. 4,795,704 and in co-pending U.S. application Ser. No. 912,595, filed Oct. 1, 1986, may be employed. The organic phase was prepared by dissolving 239.6 g (97.5% purity, 1.12 moles) of a racemic mixture of trans-3-(4-methoxyphenyl)glycidic acid methyl ester (Compound A) in 814.6 g of toluene. This organic solution was then recirculated on the shell side of a hollow fiber membrane device. Approximately twelve liters of a buffer solution (pH 8) containing 1.14 moles of sodium bisulfite, as the carbonyl adduct-forming agent, were recirculated on the lumen side of the hollow fibers.

The reaction was stopped after 23 hours and the organic fluid was drained from the membrane device. To reduce losses, the membrane device was rinsed with 500 ml of fresh toluene. The two toluene fractions were analyzed separately by HPLC to determine the concentration and enantiomeric excess of GLOP in each. The total amount of (2R,3S) ester and racemic ester was determined in the following manner:

| | Final Organic | Wash |
|---|---|---|
| 1) Total wt (grams) | 1027.70 | 421.05 |
| 2) Conc. GLOP ester (w/w) | 0.1023 | 0.0104 |
| 3) Ester wt = Total wt × conc. | 105.1 | 4.4 |
| 4) e.e (%). | 82.4 | 86.3 |
| 5) Amount (2R,3S) = Ester wt × e.e. | 86.7 | 3.8 |
| 6) Amount Racemic Ester = Ester wt.-Amt. (2R,3S) | 18.5 | 0.6 |

Total Amt. (2R,3S) = 86.66 + 3.76 = 90.42 g
Total Amt. Racemic ester = 18.47 + 0.60 = 19.07 g
Total Amt. All Esters = 105.13 + 4.36 = 109.49 g The amount of toluene required to dissolve the racemic ester at 4° C. was determined by dividing the weight of racemic ester by the solubility of the ester in toluene at this temperature (~0.13 g of racemic ester/g of toluene). The weight of toluene required was then 19.07/0.13=146.7 g. The two organic fractions were combined and toluene was then evaporated until the total weight of toluene plus ester was equal to 146.7+109.5 or 256.2 g. Afterward, the organic concentrate containing ester and toluene was cooled to 4° C. for 18 hours in order to crystallize the (2R,3S) enantiomer of the ester. The precipitated crystals were then filtered and analyzed, while the mother liquor was saved for recycling. The amount of solids collected was 91.9 g. HPLC analysis showed that the resolved ester was at least 99% pure with an enantiomeric excess of 99%. The yield of resolved ester was 38.6%.

A new experiment was started by recirculating fresh solutions of ester in toluene and aqueous buffer. A total of seven experiments were thus carried out. The results, which are summarized in Table 14, show that this batch process can produce 0.41 kg GLOP/kg of racemic glycidate ester, with the resolved GLOP having a chemical purity of 99% and an e.e. of 99%.

TABLE 14

Summary of Results from Seven Consecutive Batch Experiments

| Batch | Reaction Time (hours) | $W_r$ (g) | $W_p$ (g) | $W_c$ (g) | e.e. (%) | Recovery (%) |
|---|---|---|---|---|---|---|
| 1 | 23 | 19.1 | 90.4 | 92.1 | 99.2 | 99.9 |
| 2 | 23 | 16.5 | 96.8 | 91.3 | 99.0 | 93.4 |
| 3 | 23 | 16.3 | 93.6 | 88.6 | 98.9 | 93.6 |
| 4 | 23 | 20.4 | 92.8 | 91.2 | 99.2 | 97.5 |
| 5 | 23 | 25.2 | 87.3 | 85.5 | 99.0 | 97.0 |
| 6 | 23 | 35.1 | 91.1 | 85.6 | 98.6 | 92.6 |
| 7[a] | 30 | 41.4 | 94.6 | 86.8 | 99.0 | 90.8 |
| Total | 168 | 132.6[b] | 646.6 | 620.1 | 99.0[c] | 95.0 |

$W_r$ = weight of recycle fraction from crystallization mother liquor
$W_p$ = weight of product fraction
$W_c$ = weight of GLOP crystals
[a] Batch 7 was carried out using racemic ester which was comprised, in part, by material recycled from the first 6 batches.
[b] Amount of racemic material recovered from Batches 1–6. This mixture contained about 86% by weight racemic ester.
[c] The final product had a chemical purity of 99%.

5.4.13. EXAMPLE 29

Bench-Scale Dispersed Phase Enzymatic Resolution Providing High Optical Purity Solutions A toluene (170 mL) solution of racemic ester (31.2 g) was combined with an aqueous mixture (adjusted to pH 8) comprising $Na_2SO_3$ (9.44 g, 0.075 moles) and Lipase OF 360 (0.4 g, Meito Sangyo). The combined mixture was stirred vigorously at room temperature for 1.5 h. The dispersion was allowed to separate in a centrifuge, and the toluene phase was found to contain 14 g of optically pure (2R,3S) ester by chiral HPLC analysis. This toluene solution containing optically pure GLOP is suitable for further chemical transformations involving the GLOP and at least one other reagent. As described in the Figures, these reactions typically involve ring opening reactions accompanied by the addition of nucleophilic substances. The solution obtained from the following example (Section 5.4.14) is, likewise, useful in subsequent reactions.

It is also important to note, however, that although enriched solutions having an enantiomeric excess of about 80% or better of the desired GLOP may be suitable in subsequent transformations, samples which are only about 50% or better in its e.e. value are best crystallized, isolated, and then used in a subsequent reaction. In such a manner, 50% e.e. solutions were routinely crystallized to give selectively the (2R,3S) enantiomer having a % e.e. of 100.

5.4.14. EXAMPLE 30

Large-Scale Membrane Reactor Process Providing Organid Solutions of Highly Resolved GLOP By the procedures outlined in Section 5.4.2. (Example 19), an enzymatic membrane resolution process was carried out using a membrane having a surface area of 12 m², 150 g of Lipase OF (Meito Sangyo), 2340 g (97.5% purity, 10.96 moles) of racemic ester, and about 10 liters of toluene. The aqueous phase contained an equimolar amount of sodium bisulfite. After a reaction period of about 15 h, the organic layer was analyzed and found to contain 823 g of resolved GLOP with an enantiomeric excess of 99.0%.

5.4.15. Stability of GLOP in Some Representative Types of Solvents

It should be noted that solutions of resolved GLOP in an aromatic solvent, kept at ambient temperature over days, are stable against the loss of material or optical activity.

By contrast, a saturated methanol solution of racemic ester kept at room temperature for several days showed a marked decrease in ester content over time. After two days, HPLC analysis revealed that about 9% of the original amount of ester had degraded, presumably to the open ring compound in which the methanol is attached to the benzylic carbon. At six days, only about half of the original amount of ester remained.

In a separate experiment, the degradation rate of racemic ester was measured in a membrane reactor system using two kinds of solvent, toluene and methyl isobutyl ketone (MIBK), at different concentrations of glycidyl ester. These organic solutions were brought into contact separately with a 50 mM phosphate buffer (pH 8.0) to simulate enzymatic resolution conditions. The amount of ester present in the organic solutions was monitored over several hours. The results show that the ester in a solution of MIBK degrades with a rate constant which is about 3 times the value of the degradation rate constant of the ester in toluene.

Hence, it is apparent that the glycidyl ester is less stable in nucleophilic solvents, especially those having acidic protons like methanol. Other types of solvents which possess less nucleophilic functional groups such as MIBK, methyl t-butyl ether, diethyl ether, butyl ether, and the like, are more desirable as solvents for the enzymatic reaction and/or crystallization stages.

It has been found that relatively non-polar solvents such as dichloromethane, chloroform, freon, hexane, heptane, isooctane, cyclohexane and the like are also suitable in terms of glycidyl ester stability and solubility. As a practical matter, the minimum solubility of the enzyme substrate in the organic reaction solvent should be at least about 50 g/L. If more dilute solutions can be tolerated then the solubility of the substrate in the organic solvent is much less of an issue. The most preferred solvents appear to be non-nucleophilic aromatic solvents. Examples of these solvents include, but are not limited to, benzene, toluene, xylene, chlorobenzene, dichlorobenzene, or mixtures thereof. Toluene is particularly preferred.

As a further demonstration of the unpredictability, even unreproducibility, of crystallization experiments conducted in methanol, the following results in Table 15 is offered. As illustrated by these results, recovery of the desired material from methanol can be very good. At the same time, identical procedures provide no resolved product! By contrast, the crystallizations performed in toluene gave consistently superior results.

TABLE 15

Results of Crystallization Efforts in Methanol

| Ester weight (g) | e.e.[a] (%) | Expected $W_p$ | Recovered $W_c$ | Recovered % |
|---|---|---|---|---|
| 113.08 | 85.28 | 96.43 | 57.20 | 59.3 |
| 114.01 | 87.50 | 25.10 | 21.67 | 86.3 |
|  |  | 25.10 | 18.02 | 71.8 |
|  |  | 50.20 | 0.00 | 0.0 |
| 113.56 | 84.40 | 23.96 | 21.42 | 89.4 |
|  |  | 23.96 | 15.50 | 64.7 |
|  |  | 23.96 | 21.89 | 91.4 |
|  |  | 23.96 | 0.00 | 0.0 |
| 113.38 | 84.30 | 23.89 | 6.88 | 28.8 |
|  |  | 23.89 | 22.69 | 95.0 |
|  |  | 23.89 | 25.09 | 105.0 |
|  |  | 23.89 | 19.33 | 80.9 |
| 108.73 | 84.36 | 22.93 | 22.29 | 97.2 |
|  |  | 22.93 | 11.63 | 50.7 |
|  |  | 22.93 | 20.00 | 87.2 |
|  |  | 22.93 | 20.62 | 89.9 |
| 110.18 | 84.15 | 23.17 | 22.25[b] | 96.0 |
|  |  | 23.17 | 0.00 | 0.0 |
|  |  | 23.17 | 0.00 | 0.0 |
|  |  | 23.17 | 18.79[b] | 81.1 |
| 117.15 | 80.43 | 23.55 | 21.13[b] | 89.7 |
|  |  | 70.65 | 61.38[b] | 86.9 |

[a]These values reflect the e.e. of the substrate in solution.
[b]These crystallizations were carried out in toluene solvent.

5.5. Further Considerations with Regard to Choice of Solvent

It has already been shown that the organic phase provides some degree of protection for the substrate molecule against hydrolysis of both the ester and epoxide functions. Such protection extends to all stereoisomers of the 3-(4-methoxyphenyl)glycidic acid methyl ester, not only to the racemic substrate. However, the choice of solvent as the organic phase in the multi-phase reaction may also affect the activity, both in the rate of reaction and in the stereoselectivity, of the enzyme catalyst. Additional studies were undertaken to elucidate the effects of several types of solvents in the performance of some model enzymes.

5.5.1. The Effect of Solvent on Enzyme Activity

To determine if the composition of the organic phase affects the activity of a given enzyme, a number of organic solvents were chosen, including a water-miscible organic solvent, 1,4-dioxane. The effect of a change in pH was also considered in these experiments. Two enzymes, Lipase M-AP (Amano Enzyme Corp.) and Lipase OF 360 (Meito Sangyo) were chosen for this study. A general procedure for generating this data is described below:

Racemic 3-(4-methoxyphenyl)glycidic acid methyl ester (10.0 mmol, 2.08 g) was dissolved in 50 mL of the chosen organic solvent. This solution was subsequently added to 50 mL of 200 mM sodium phosphate buffer at the chosen pH, either pH 7.0 or pH 8.0, in a 250 mL shaker flask. The chosen commercial enzyme preparation (100 mgs), either Lipase M-AP or Lipase OF 360, was then added. The flask was closed and agitated for 18 hours at ambient temperature (20–25° C.). The reaction mixture was then poured into a separatory funnel, the organic layer removed (except in the case of 1,4-dioxane, which is miscible in water), and the aqueous layer washed with diethyl ether. The organic layers were then combined, backwashed with water, and dried over anhydrous magnesium sulfate. The organic solvent was evaporated under reduced pressure. The recovered ester was then weighed and checked for optical purity (enantiomeric excess or e.e.) without further purification. The optical activities of the ester materials recovered from the enzymatic reactions were determined in ethanol at c=1.0, for which a value of $[\alpha]_D = -196.2°$ was used for an e.e. of 100% for the (2R,3S) isomer. The enantioselectivity value $E_{app}$ is the calculated E value, uncorrected for non-enzymatic non-specific degradation of the substrate. A value calculated to be over 50 is arbitrarily denoted as "large".

The results obtained using this procedure, as applied to various enzyme/pH/organic solvent combinations, are listed in the following Tables.

TABLE 16

Stereospecific Hydrolysis of 3-(4-Methoxyphenyl)glycidic Acid Methyl Ester by Lipase OF 360 at pH 7.0

| Organic Phase | Percent hydrolysis | $[\alpha]_D$ | % e.e. | $E_{app}$ |
|---|---|---|---|---|
| cyclohexane | 61.5 | −1.1 | 0.6 | 1.0 |
| 1,4-dioxane | 56.3 | −10.3 | 5.2 | 1.1 |
| Me$^t$BuO | 54.8 | −28.5 | 14.5 | 1.4 |
| CHCl$_3$ | 20.7 | −21.1 | 10.8 | 2.7 |
| CCL$_4$ | 30.3 | −10.0 | 5.1 | 1.3 |
| toluene | 45.7 | −59.7 | 30.4 | 2.8 |
| MIBK | 22.1 | −60.4 | 30.8 | large |
| benzene | 70.7 | −105.3 | 53.7 | 2.5 |
| p-xylene | 42.8 | −39.7 | 20.2 | 2.1 |

TABLE 17

Stereospecific Hydrolysis of 3-(4-Methoxyphenyl)glycidic Acid Methyl Ester by Lipase OF 360 at pH 8.0

| Organic Phase | Percent hydrolysis | $[\alpha]_D$ | % e.e. | $E_{app}$ |
|---|---|---|---|---|
| cyclohexane | 56.7 | −2.3 | 1.2 | 1.0 |
| 1,4-dioxane | 16.8 | −5.1 | 2.6 | 1.3 |
| Me$^t$BuO | 42.3 | −46.6 | 23.8 | 2.4 |
| CHCl$_3$ | 11.1 | −11.1 | 5.7 | 2.8 |
| CCL$_4$ | 42.3 | −41.9 | 21.4 | 2.2 |
| toluene | 27.9 | −94.5 | 48.2 | large |
| MIBK | 38.5 | −83.6 | 42.6 | 7.9 |
| benzene | 37.7 | −99.5 | 50.7 | 18.7 |
| p-xylene | 35.1 | −104.6 | 53.3 | large |

TABLE 18

Stereospecific Hydrolysis of 3-(4-Methoxyphenyl)glycidic Acid Methyl Ester by Lipase M-AP at pH 7.0

| Organic Phase | Percent hydrolysis | $[\alpha]_D$ | % e.e. | $E_{app}$ |
|---|---|---|---|---|
| cyclohexane | 64.4 | −1.3 | 0.7 | 1.0 |
| 1,4-dioxane | 34.1 | −0.3 | −0 | 1.0 |
| Me$^t$BuO | 47.1 | −47.3 | 24.1 | 2.2 |
| CHCl$_3$ | 16.8 | −3.2 | 1.6 | 1.0 |
| CCL$_4$ | 47.1 | −51.8 | 26.4 | 2.3 |
| toluene | 38.9 | −85.8 | 43.7 | 8.2 |

TABLE 18-continued

Stereospecific Hydrolysis of 3-(4-Methoxyphenyl)glycidic Acid Methyl Ester by Lipase M-AP at pH 7.0

| Organic Phase | Percent hydrolysis | $[\alpha]_D$ | % e.e. | $E_{app}$ |
|---|---|---|---|---|
| MIBK | 28.8 | −91.1 | 46.4 | large |
| benzene | 34.6 | −93.7 | 47.8 | 31.6 |
| p-xylene | 41.8 | −65.4 | 33.3 | 4.2 |

TABLE 19

Stereospecific Hydrolysis of 3-(4-Methoxyphenyl)glycidic Acid Methyl Ester by Lipase M-AP at pH 8.0

| Organic Phase | Percent hydrolysis | $[\alpha]_D$ | % e.e. | $E_{app}$ |
|---|---|---|---|---|
| cyclohexane | 65.9 | −1.4 | 0.7 | 1.0 |
| 1,4 dioxane | 19.2 | −0.4 | −0 | 1.3 |
| Me$^t$BuO | 49.5 | −40.3 | 20.5 | 1.8 |
| CHCl$_3$ | 19.2 | −0.4 | −0 | 1.0 |
| CCL$_4$ | 47.1 | −49.0 | 25.0 | 2.2 |
| toluene | 30.3 | −78.5 | 40.0 | 35.6 |
| MIBK | 15.9 | −38.7 | 19.7 | large |
| benzene | 37.5 | −104.2 | 53.1 | 27.8 |
| p-xylene | 41.8 | −69.7 | 35.5 | 3.7 |

5.5.2. Determination of the Non-Enzymatic Degradation of Substrate Ester

Following these experiments, another factor was then considered. As the interfacial activity of any compound will be affected by surfactants, for instance a protein, one could expect the presence of the enzyme to exert effects on the non-enzymatic nonspecific degradation of the substrate compound. To test this proposition, control experiments were run in which bovine serum albumin (BSA) was substituted for the hydrolytic enzyme in the reaction mixture. The chlorinated hydrocarbons and p-xylene were omitted for convenience. The general method for obtaining this data is described below:

Racemic 3-(4-methoxyphenyl) glycidic acid methyl ester (10.0 mmols, 2.08 g) was dissolved in 50 mL of the chosen organic solvent, and added to 50 mL of 200 mM sodium phosphate buffer at the chosen pH (7.0, 8.0, or 8.5) in a 250 mL shaker flask. Bovine serum albumin (BSA, 100 mg) was then added. The flask was closed, and agitated for 18 hours at ambient temperature (20–25° C.). The reaction mixture was then poured into a separatory funnel, the organic layer removed (except in the case of 1,4-dioxane, which is miscible in water), and the aqueous layer washed with diethyl ether. The organic layers were then combined, backwashed with water, and dried over anhydrous magnesium sulfate. The organic solvent was then removed under reduced pressure, and the recovered ester weighed to determine the extent of non-enzymatic degradation.

The results of these experiments, applied to various BSA/pH/organic solvent combinations, are listed in Table 20.

TABLE 20

Determination of Non-enzymatic Degradation of 3-(4-methoxyphenyl)glycidic Acid Methyl Ester in the Presence of BSA

| Organic Phase | Percent degradation | | |
|---|---|---|---|
| | pH 7.0 | pH 8.0 | pH 8.5 |
| cyclohexane | 71.6 | 38.5 | |
| 1,4-dioxane | 40.9 | 21.6 | |
| Me$^t$BuO | 41.8 | 22.1 | |
| toluene | ND | 14.3 | 19.1 |
| MIBK | ND | 15.0 | 12.0 |
| benzene | 38.5 | 14.4 | |

Using this data, it was then possible to correct the data presented in Tables 16–19 to reflect only the rate and specificity of the enzyme catalysed hydrolysis of the substrate. This corrected data are listed in the following Tables.

TABLE 21

Corrected Conversion and Enantioselectivity Values for Lipase OF 360

| Organic Phase | Percent Conversion | | $E_{cor}$ | |
|---|---|---|---|---|
| | pH 7.0 | pH 8.0 | pH 7.0 | pH 8.0 |
| cyclohexane | 0 | 18.2 | 1.9 | 1.0 |
| 1,4-dioxane | 15.4 | 0 | 5.1 | |
| Me$^t$BuO | 18.7 | 20.2 | | 40.9 |
| toluene | ND | 13.6 | | large |
| MIBK | ND | 23.5 | | large |
| benzene | 32.2 | 23.3 | large | large |

TABLE 22

Corrected Conversion and Enantioselectivity Values for LIPASE M-AP

| Organic Phase | Percent Conversion | | $E_{cor}$ | |
|---|---|---|---|---|
| | pH 7.0 | pH 8.0 | pH 7.0 | pH 8.0 |
| cyclohexane | 0 | 27.4 | | 1.0 |
| 1,4-dioxane | 0 | 0 | large | |
| Me$^t$BUO | 5.3 | 27.4 | large | 4.1 |
| toluene | ND | 16.0 | | large |
| MIBK | ND | 1.0 | | large |
| benzene | 0 | 23.1 | | large |

From the preceding data it may be seen that the three organic solvents, MIBK, benzene and toluene, provide an attractive aqueous/organic solvent interface with physiochemical characteristics that give the highest observed enantioselectivity with both Lipase M-AP and Lipase OF 360. The data show that MIBK and toluene provide nearly the same degree of protection against non-enzyme catalyzed degradation of substrate.

5.6. Post-Enzyme Resolution Clean-Up of Crude Reaction Products by Extraction with a Carbonyl Adduct-Forming Agent Although the preferred method of carrying out an efficient enzymatic resolution of racemic substrate involves a multiphase system in which the carbonyl adduct-forming agent is already present in the aqueous phase, it may not be possible in certain situations (e.g., extreme sensitivity of the enzyme to the adduct-forming agent) to perform the resolution under these preferred conditions.

It has been found surprisingly that in the case of the enantioselective ester hydrolysis of Compound A (GLOP), the hydrolysis by-product, p-(methoxy) phenylacetaldehyde, can be removed successfully simply by extracting the crude organic solution with an aqueous solution of the carbonyl adduct-forming agent. Even more startling, is the discovery that such a "washing" step gives rise to a resolved product, which remains in the organic layer, having a higher optical activity as measured by the optical rotation of the washed solution relative to the untreated initial crude organic layer.

Moreover, because the addition of the carbonyl adduct-forming agent is usually reversible, the carbonyl by-product may be recovered from the aqueous wash and utilized for a separate purpose. The bisulfite adducts and Schiff bases may be readily decomposed under acidic conditions, for instance, and the organic solvent-soluble carbonyl compound may thus be recovered from the water layer by a simple organic solvent extraction step.

The foregoing aspects of the present invention are best illustrated by the following example.

5.6.1. EXAMPLE 34

Purification of Crude Organic Solution by Extraction with Aqueous Bisulfite Anion Toluene (50 mL) containing 10 mmol of racemic Compound A was shaken with 50 mL of 0.2 M sodium phosphate buffer at pH 8.0, containing 100 mg of the commercial enzyme preparation from Amano known as Lipase M-AP, for 18 hours at ambient temperature. The reaction mixture was then diluted with water to a volume of 400 mL, and extracted twice with 400 mL of diethyl ether. The combined organic phases were then backextracted with water (2×400 mL), dried over magnesium sulphate, and evaporated to leave 1.5 g (7.2 mmol) of crude product material. The optical rotation of this material in ethanol at c=1.0 was −68.0°, indicating an enantiomeric excess of 34.7%. The value of −196.2° for the optical rotation is equivalent to the (2R,3S) isomer as measured in ethanol. The crude product was then redissolved in 300 mL of diethyl ether, and the organic solution washed twice with 100 mL of a 10% sodium bisulfite solution. The organic phase was then backwashed with water, dried over magnesium sulphate, and evaporated to leave 1.4 g (6.7 mmol) of the washed product material. The optical rotation of this material is ethanol at c=1.0 was −117.5°, indicating an enantiomeric excess of 59.9% of the desired Compound A.

It was found, however, that a 10% bisulfite solution would also attack the epoxide function of compound A in the absence of any other potential electrophile, thus leading to a loss of Compound A during reaction work-up. This potential problem was illustrated by an experiment in which 2.0 g of pure racemic compound were dissolved in diethyl ether (200 mL) and extracted once with 250 mL of an aqueous 10% bisulfite solution. The organic layer was then worked up as usual to yield 1.8 g of racemic Compound A. An aqueous wash in the absence of bisulfite provides a nearly quantitative recovery of starting racemate.

It should also be noted that numerous other reagents may serve as effective carbonyl adduct-forming agents. These compounds may be water-miscible and may preferably be ionizable or capable of supporting a charge. In addition to the adducts formed with bisulfite, other adducts such as Schiff bases, oximes, hydrazones, carbazones, acetals, thiocetals, imidazolines, hydroxylimines, halohydrins, cyanohydrins, aminonitriles, and the like may be formed which may have solvent phase partition coefficients more favorable to the aqueous layer. Most advantageously, such adducts may be designed to support a change and, thus, increase its solubility in the aqueous layer. Representative examples of such adduct-forming agents include, but are not limited to, Girard's Reagents, N-(carboxymethyl) pyridimium chloride hydrazide, (carboxymethyl) trimethylammonium chloride hydrazide, N,N-dimethylhydrazine, semicarbazides, hydroxylamines, and amino acids, to name a few.

5.7. Reactivity of the Oxirane Ring

It should be apparent that the lability of the epoxide ring in the glycidyl ester substrate pervades each stage of the multi-step process for securing a good yield of a resolved high optical purity product. At each stage of this process, the present invention has discovered conditions in which the epoxide ring is preserved until such time as a deliberate ring-opening reaction, preferably one which proceeds in a stereochemically predictable fashion, is contemplated. Thus, beginning with the multi-phase reaction conditions, the identification of suitable organic reaction solvents, crystallization conditions, purification of crude mixtures, and subsequent utilization of the homochiral intermediates, this invention has exceeded all of its objectives. In addition, the present invention provides a large-scale process for the production of optically active glycidyl ester intermediates which is unparalleled both in its economy and convenience.

As discussed previously, these intermediates may be employed as recrystallized materials or, quite conveniently, in solution as obtained from the resolution process. The chemistry of these subsequent transformations, although not stressed in the present discussion, is of vital importance nonetheless. For a more detailed description of the subsequent chemical transformations involving the chiral intermediates of interest, the reader is referred to existing references such as: U.S. Pat. No. 4,420,628 issued to Inoue et al. (especially the discussion on Lewis-acid-catalyzed ring opening of the oxirane); Hashiyama et al. in *J. Chem. Soc. Perkin Trans.* 1 1984, 1725 and in Ibid. 1985, 421 (stereo- and regiochemical considerations in the reaction of GLOP with thiophenols). The full disclosures of these references are incorporated herein by reference.

The present invention is not intended to be limited in scope by the above experiments or by the reactants, solvents, solutions, membranes, or catalysts used since each is intended merely as an illustration of the invention. In addition, functional equivalents of the claimed methods utilized and set forth herein are intended to be within the scope of this invention. Indeed, various modifications of the invention, in addition to those shown and described herein, will become apparent to those skilled in the art from the foregoing description and accompanying specification. Such modifications are intended to fall within the scope of the appended claims.

What is claimed is:

1. A method for obtaining an organic solution comprising an optically active diastereomer of a trans-glycidic acid ester compound of the formula I

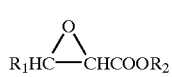

(I)

in which $R_1$ is a phenyl or substituted phenyl and $OR_2$ is a group derived from an alcohol, which method comprises:

(a) preparing an organic solution comprising a diastereomer of a compound of formula I dissolved in a water-immiscible organic solvent, said diastereomer present as a mixture of a first and a second enantiomer; and (b) contacting said organic solution of said diastereomer with an aqueous mixture comprising water and a suitable hydrolytic enzyme, said enzyme being capable of catalyzing the enantioselective hydrolysis of said first enantiomer, under conditions effective to provide an organic solution enriched in said second enantiomer.

2. The method of claim 1 which further comprises separating said organic solution enriched in said second enantiomer from said aqueous mixture.

3. The method of claim 1 which further comprises isolating from said enriched organic solution said second enantiomer.

4. The method of claim 3 in which said second enantiomer is isolated from said enriched organic solution by crystallization.

5. The method of claim 4 in which said second enantiomer is present in said organic solution with an enantiomeric excess of about 50% or better.

6. The method of claim 1 which further comprises utilizing said organic solution enriched in said second enantiomer in a subsequent chemical transformation involving said second enantiomer and at least one additional reagent.

7. The method of claim 6 in which said second enantiomer is present in said organic solution with an enantiomeric excess of about 80% or better.

8. The method of claim 6 in which said chemical transformation involves a ring opening reaction of said second enantiomer.

9. The method of claim 8 in which said ring opening reaction is promoted by acid.

10. The method of claim 6 in which said additional reagent is nucleophilic.

11. The method of claim 6 in which said additional reagent is ortho-aminothiophenol.

12. The method of claim 6 in which said additional reagent is ortho-nitrothiophenol.

13. The method of claim 1 in which said water-immiscible organic solvent is non-nucleophilic.

14. The method of claim 1 in which said water-immiscible organic solvent is a non-nucleophilic aromatic solvent.

15. The method of claim 1 in which said water-immiscible organic solvent is halogenated.

16. The method of claim 1 in which said water-immiscible organic solvent is a halogenated non-nucleophilic solvent.

17. The method of claim 1 in which said water-immiscible organic solvent is a chlorinated non-nucleophilic aromatic solvent.

18. The method of claim 1 in which said water-immiscible organic solvent is selected from the group consisting of benzene, toluene, xylene, chlorobenzene, dichlorobenzene, methyl isobutyl ketone, methyl t-butyl ether, diethyl ether, dichloromethane, chloroform, hexane, heptane, isooctane, cyclohexane, and mixtures thereof.

19. The method of claim 1 in which said water-immiscible organic solvent is toluene.

20. The method of claim 1 wherein said enzyme is selected from the group consisting of proteases, esterases, and lipases.

21. The method of claim 1 wherein said enzyme is a lipase.

22. The method of claim 1 wherein said enzyme is provided in a form selected from the group consisting of purified enzyme, partially purified enzyme, cell extract, cell lysate, and whole cells.

23. The method of claim 1 wherein said enzyme is derived from a microorganism.

24. The method of claim 22 wherein said microorganism is selected from the group consiting of genus Mucor, genus Candida, genus Pseudomonas, genus Bacillus, and genus Aspergillus.

25. The method of claim 22 wherein said enzyme is a lipase from genus Candida.

26. The method of claim 22 wherein said hydrolytic enzyme is a lipase from Candida cylindracea.

27. The method of claim 1 wherein said enzyme is derived from a mammal.

28. The method of claim 26 wherein said hydrolytic enzyme is selected from the group consisting of porcine liver esterase, porcine pancreatic lipase, trypsin, chymotrypsin, pancreatin, and cholesterol esterase.

29. The method of claim 1 wherein said diastereomer is a trans-glycidic acid ester compound of formula I.

30. The method of claim 1 wherein $R_1$ is a 4-methoxyphenyl group.

31. The method of claim 1 wherein $R_2$ is a methyl group.

32. The method of claim 1 wherein said diastereomer is trans-3-(4-methoxyphenyl) glycidic acid methyl ester.

33. The method of claim 31 wherein said first enantiomer is (2S,3R)-trans-3-(4-methoxyphenyl) glycidic acid methyl ester.

34. The method of claim 31 wherein said second enantiomer is (2R,3S)-trans-3-(4-methoxyphenyl) glycidic acid methyl ester.

35. The method of claim 1 wherein said organic solution and said aqueous mixture are brought into contact in step (b) by means of forming a dispersion of one of said organic solution or aqueous mixture within the other.

36. The method of claim 35 wherein said dispersion is contained in a reactor selected from the group consisting of a stirred-tank reactor, packed-bed reactor, and fluidized-bed reactor.

37. The method of claim 35 which further comprises recovering said enzyme from said dispersion.

38. A method for obtaining an organic solution comprising an optically active trans-3-(aryl) glycidic acid ester compound of the formula I $$R_1HC\underset{\diagdown\diagup}{\overset{O}{\phantom{X}}}CHCOOR_2 \qquad (I)$$

in which $R_1$ is a phenyl or substituted phenyl and $OR_2$ is a group derived from an alcohol, which method comprises:

(a) preparing an organic solution comprising a trans-3-(aryl) glycidic acid ester compound of formula I dissolved in a non-nucleophilic water-immiscible aromatic solvent, said compound present as a mixture of a first and a second enantiomer; and (b) contacting said organic solution of said compound with an aqueous mixture comprising water and a suitable hydrolytic enzyme, said enzyme being capable of catalyzing the enantioselective hydrolysis of said first enantiomer, under conditions effective to provide an organic solution enriched in said second enantiomer.

39. A method for resolving a racemic mixture of a trans-glycidic acid ester compound of the formula II

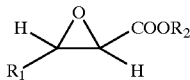

in which $R_1$ is a phenyl or substituted phenyl and $OR_2$ is a group derived from an alcohol, which method comprises:
(a) providing an organic solution comprising a water-immiscible organic solvent and a racemic compound of formula II present as a mixture of a first and a second stereoisomer; and
(b) contacting said organic solution of first and second stereoisomers with an aqueous mixture comprising water and a suitable hydrolytic enzyme capable of catalyzing the stereoselective hydrolysis of said first stereoisomer,
under conditions effective to provide an organic solution enriched in said second stereoisomer.

40. The method of claim 39 which further comprises utilizing said substantially resolved second stereoisomer in a subsequent chemical transformation.

41. The method of claim 40 in which the end product of said subsequent chemical transformation is diltiazem.

42. A method for resolving a racemic mixture of a trans-glycidic acid ester compound of the formula II

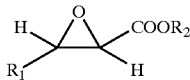

wherein $R_1$ is selected from the group consisting of phenyl or substituted phenyl and $OR_2$ is a group derived from an alcohol, the method comprising:
(a) providing an aqueous mixture comprising water and a racemic compound of formula II present as a mixture of a first and a second stereoisomer; and
(b) contacting said aqueous mixture of first and second stereoisomers with a suitable hydrolytic enzyme, wherein said enzyme catalyzes the stereoselective hydrolysis of said first stereoisomer, leaving said second stereoisomer in a substantially resolved form.

43. The method of claim 42 which further comprises isolating from said aqueous mixture said substantially resolved second stereoisomer.

44. The method of claim 1, 38, 43, or 42 which further comprises recovering any non-ester carbonyl-containing by-products which may be present.

45. The method of claim 1, 38, 39 or 45 which further comprises recovering any non-ester carbonyl-containing by-products which may be present in said organic solution, which recovery comprises (a) selectively crystallizing from an isolated solution of said second stereoisomer and any said non-ester carbonyl-containing by-products, in a suitable solvent, said second stereoisomer thereby leaving a mother liquor of said isolated solution substantially enriched in any said non-ester carbonyl containing by-products; and (b) separating said mother liquor from said recrystallized second stereoisomer.

46. The method of claim 47 in which said suitable solvent is methanol.

47. The method of claim 44 which further comprises utilizing any said non-ester carbonyl-containing by-products or adducts thereof separately.

48. The method of claim 47 in which any said non-ester carbonyl-containing by-products or adducts thereof are utilized in a subsequent chemical transformation.

49. The method of claim 48 in which the end product of said subsequent chemical transformation is phenylacetic acid or a substituted phenylacetic acid.

50. The method of claim 38, 39, or 42 in which said non-ester carbonyl-containing by-product is phenylacetaldehyde or a substituted phenylacetaldehyde.

51. The method of claim 50 in which said non-ester carbonyl-containing by-product is 4-methoxyphenylacetaldehyde.

52. The method of claim 48 in which the end product of said subsequent chemical transformation is 4-methoxyphenylacetic acid.

53. The method of claim 45 in which said suitable solvent is a selected from the group consisting of methyl isobutyl ketone, methyl t-butyl ether, diethyl ether and butyl ether.

54. The method of claim 45 in which said suitable solvent is a non-nucleophilic aromatic solvent.

55. The method of claim 54 in which said non-nucleophilic aromatic solvent is toluene.

56. The method of claim 44 in which said recovery includes selective crystallization.

57. A method for stereoselectively hydrolyzing an ester bond of a trans-glycidic acid ester compound of formula II:

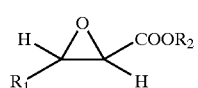

wherein $R_1$ is selected from the group consisting of phenyl and substituted phenyl and $OR_2$ is a group derived from an alcohol, comprising contacting a racemic compound of formula II with a hydrolytic enzyme capable of catalyzing the stereoselective hydrolysis of a compound of formula II, thereby stereoselectively hydrolyzing an enantiomer of said racemic compound of formula II.

58. The method of claim 53 which further comprises separating the non-hydrolyzed enantiomer from the hydrolysis product.

59. The method of claim 53 wherein said contacting step is carried out in a composition comprising an organic solvent and water.

60. The method of claim 55 wherein said organic solvent is selected from the group consisting of toluene, methyl t-butyl ether, hexane, cyclohexane, heptane, methyl isobutyl ketone and ethyl acetate.

61. The method of claim 56 wherein said organic solvent is toluene.

62. The method of claim 53 wherein said enzyme is selected from the group consisting of proteases, esterases and lipases.

63. The method of claim 58 wherein said enzyme is a lipase.

64. The method of claim 53 wherein $R_1$ is a 4-methoxyphenyl group and $R_2$ is a methyl group.

65. An aqueous composition comprising:
(a) a composition selected from the group consisting of:
(i) the enantiomers of a trans-glycidic acid ester compound of formula II:

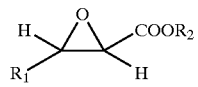

wherein $R_1$ is selected from group consisting of phenyl and substituted phenyl and $OR_2$ is a group derived from an alcohol, and (ii) an enantiomer of a trans-glycidic acid ester compound of formula II and the hydrolysis product of the other of said enantiomer, and (b) a hydrolytic enzyme capable of catalyzing the stereoselective hydrolysis of one of the enantiomers of formula II.

66. The aqueous composition of claim 65 which further comprises an organic solvent.

67. The aqueous composition of claim 66 wherein said organic solvent is selected from the group consisting of toluene, methyl t-butyl ether, hexane, cyclohexane, heptane, methyl isobutyl ketone and ethyl acetate.

68. The aqueous composition of claim 67 wherein said organic solvent is toluene.

69. The aqueous composition of claim 65 wherein said enzyme is selected from the group consisting of proteases, esterases and lipases.

70. The composition of claim 65 wherein $R_1$ is a 4-methoxyphenyl group and $R_2$ is a methyl group.

71. The method of claim 57 wherein the 2S, 3R enantiomer is hydrolyzed.

72. The aqueous composition of claim 61 wherein the hydrolysis product is the 2S, 3R enantiomer.

* * * * *

UNITED STATES PATENT AND TRADEMARK OFFICE
CERTIFICATE OF CORRECTION

PATENT NO. : 6,521,445 B1
DATED : February 18, 2003
INVENTOR(S) : Dobbs et al.

It is certified that error appears in the above-identified patent and that said Letters Patent is hereby corrected as shown below:

Column 46,
Lines 5 and 9, please replace "22" with -- 23 --;
Line 11, please replace "22" with -- 23 -- and delete with word "hydrolytic";
Line 15, please delete the word "hydrolytic";
Lines 27 and 30, please replace "31" with -- 32 --;

Column 47,
Line 47, please replace "43" with -- 39 --;
Line 50, please replace "1, 38, 39 or 45" with -- 1, 38 or 39 --;
Line 60, please replace "47" with -- 45 --;

Column 48,
Line 4, please insert -- 1, -- after the word "claim"; and

Column 50,
Line 10, please replace "61" with -- 65 --.

Signed and Sealed this

Second Day of September, 2003

JAMES E. ROGAN
*Director of the United States Patent and Trademark Office*